(12) United States Patent
Murata

(10) Patent No.: US 11,129,528 B2
(45) Date of Patent: Sep. 28, 2021

(54) OCT APPARATUS

(71) Applicant: NIDEK CO., LTD., Aichi (JP)

(72) Inventor: Keiji Murata, Toyama (JP)

(73) Assignee: NIDEK CO., LTD., Aichi (JP)

( * ) Notice: Subject to any disclaimer, the term of this patent is extended or adjusted under 35 U.S.C. 154(b) by 109 days.

(21) Appl. No.: 16/145,982

(22) Filed: Sep. 28, 2018

(65) Prior Publication Data

US 2019/0099074 A1  Apr. 4, 2019

(30) Foreign Application Priority Data

Sep. 29, 2017  (JP) .............................. JP2017-191601

(51) Int. Cl.
| | | |
|---|---|---|
| *A61B 3/10* | (2006.01) | |
| *A61B 3/14* | (2006.01) | |
| *G01B 9/02* | (2006.01) | |
| *A61B 3/117* | (2006.01) | |
| *A61B 3/00* | (2006.01) | |

(Continued)

(52) U.S. Cl.
CPC ................ *A61B 3/102* (2013.01); *A61B 3/14* (2013.01); *G01B 9/02004* (2013.01); *G01B 9/02028* (2013.01); *G01B 9/02091* (2013.01); *A61B 3/0025* (2013.01); *A61B 3/1025* (2013.01); *A61B 3/117* (2013.01); *A61B 3/1173* (2013.01);

(Continued)

(58) Field of Classification Search
CPC ..... A61B 3/102; A61B 3/0025; A61B 5/0066; A61B 3/14; A61B 3/1025; A61B 3/117; A61B 3/1173; A61B 3/12; A61B 3/1005; A61B 3/1233; A61B 3/152; A61B 3/0008; A61B 3/0016; A61B 5/7239

USPC ........ 351/200, 205–206, 209–211, 221–223, 351/243–246

See application file for complete search history.

(56) References Cited

U.S. PATENT DOCUMENTS

| | | |
|---|---|---|
| 5,493,109 A | 2/1996 | Wei et al. |
| 6,004,314 A | 12/1999 | Wei et al. |
| (Continued) | | |

FOREIGN PATENT DOCUMENTS

| | | |
|---|---|---|
| JP | 8-66421 A | 3/1996 |
| JP | 2005-525893 A | 9/2005 |
| (Continued) | | |

OTHER PUBLICATIONS

Communication dated Mar. 11, 2019, issued by the European Patent Office in counterpart European Application No. 18197439.5.

(Continued)

*Primary Examiner* — Brandi N Thomas
(74) *Attorney, Agent, or Firm* — Sughrue Mion, PLLC

(57) ABSTRACT

An OCT apparatus includes an OCT optical system that splits light from an OCT light source into a measurement optical path and a reference optical path and detects a spectral interference signal between measurement light and reference light, an image processor that processes the spectral interference signal to acquire OCT data of an examinee's eye, an optical scanner that deflects the measurement light and performs scanning on tissue of the examinee's eye, and a light guiding optical system that includes an objective optical system curving a concentrating plane such that the concentrating plane has a convex shape toward a side of a fundus, and forms the concentrating plane of the measurement light in an anterior chamber.

14 Claims, 18 Drawing Sheets

(51) Int. Cl.
*G01N 21/47* (2006.01)
*G02B 27/10* (2006.01)

(52) U.S. Cl.
CPC ...... *G01B 2290/70* (2013.01); *G01N 21/4795* (2013.01); *G02B 27/106* (2013.01)

(56) References Cited

U.S. PATENT DOCUMENTS

| | | |
|---|---|---|
| 2003/0218755 A1 | 11/2003 | Wei et al. |
| 2009/0268161 A1* | 10/2009 | Hart ................... A61B 3/102 |
| | | 351/208 |
| 2010/0067020 A1 | 3/2010 | Podoleanu |
| 2011/0096291 A1 | 4/2011 | Buckland et al. |
| 2011/0102802 A1 | 5/2011 | Izatt et al. |
| 2011/0228221 A1 | 9/2011 | Hanebuchi et al. |
| 2012/0140173 A1 | 6/2012 | Uhlhorn et al. |
| 2013/0100406 A1 | 4/2013 | Buckland et al. |
| 2013/0329188 A1 | 12/2013 | Buckland et al. |
| 2014/0160431 A1 | 6/2014 | Izatt et al. |
| 2014/0300902 A1 | 10/2014 | Buckland et al. |
| 2014/0354950 A1* | 12/2014 | Buckland ............ A61B 3/1025 |
| | | 351/206 |
| 2016/0166144 A1 | 6/2016 | Izatt et al. |
| 2016/0317028 A1* | 11/2016 | Murata ................ A61B 3/1225 |

FOREIGN PATENT DOCUMENTS

| | | |
|---|---|---|
| JP | 2011-215134 A | 10/2011 |
| JP | 2016-32578 A | 3/2016 |
| JP | 2016-209577 A | 12/2016 |
| WO | 2008000078 A1 | 1/2008 |
| WO | 2011050249 A1 | 4/2011 |

OTHER PUBLICATIONS

Office Action dated Jun. 29, 2021 by the Japanese Patent Office in counterpart Japanese Patent Application No. 2017-191601.

* cited by examiner

First OCT data

ZD1

Second OCT data

ZD2

<Anterior Chamber Imaging Mode>

<Fundus imaging mode>

OCT APPARATUS

CROSS-REFERENCE TO RELATED APPLICATION

This application claims priority from Japanese Patent Application No. 2017-191601 filed on Sep. 29, 2017, the entire subject-matter of which is incorporated herein by reference.

TECHNICAL FIELD

This disclosure relates to an OCT apparatus that obtains OCT data of a subject (for example, an eye).

BACKGROUND

For example, in the field of ophthalmology, in recent years, an OCT apparatus that processes a spectral interference signal output from an OCT optical system so as to acquire a tomogram. For example, JP-A-2016-209577 discloses an apparatus that sets an optical position of an optical scanner at a focal position of an objective optical system so as to acquire a tomogram of an anterior chamber.

The present inventors have attempted to acquire a tomogram of an anterior chamber, with a wide range in a depth direction as an imaging range and, as a result, have found technical problems exemplified below.

For example, in a case where a concentrating position of a measurement light is fixed at a certain depth (that is, a concentrating plane becomes a flat plane), it is difficult to obtain a tomogram of good depiction in a wide range from a cornea to a crystalline lens. To be more specific, in a case where the concentrating plane is set at a deep position with reference to the crystalline lens, light radiating peripheral portions such as an iris or an anterior chamber angle are not concentrated in regions of the peripheral portions. Therefore, sensitivity is relatively low. As a result, it is not possible to obtain a clear tomogram. In addition, since the beams are blocked by the iris before being concentrated, a beam intensity is useless, and thus it is easy to generate a noise signal such as an artifact. On the other hand, in a case where the concentrating plane is set at a shallow position of the anterior chamber angle or the like, a worse photograph of the crystalline lens having low beam-reaching intensity originally is acquired due to an influence of scattering or the like of the beams by tissue.

SUMMARY

An object of the disclosure is to provide an OCT apparatus that enables to acquire a tomogram having high image quality or resolution in a wide range of an anterior chamber in a depth direction.

An OCT apparatus of the disclosure has the following configuration.

An OCT apparatus including:
an OCT optical system that causes an optical splitter to split light from an OCT light source into a measurement optical path and a reference optical path, and detects a spectral interference signal between measurement light guided to an examinee's eye through the measurement optical path and reference light from the reference optical path;
an image processor that processes the spectral interference signal output from the OCT optical system to acquire OCT data of the examinee's eye;
an optical scanner that deflects the measurement light from the optical splitter, and performs scanning on tissue of the examinee's eye; and
a light guiding optical system that includes an objective optical system, guides the measurement light from the optical splitter to the examinee's eye through the objective optical system, and forms a concentrating plane of the measurement light in an anterior chamber of the examinee's eye,
in which the objective optical system curves the concentrating plane such that the concentrating plane has a convex shape toward a side of a fundus of the examinee's eye.

According to the disclosure, it is possible to acquire a tomogram having high image quality or resolution in a wide range of an anterior chamber in a depth direction.

DETAILED DESCRIPTION

Overview

Hereinafter, embodiments of this disclosure will be described. Hereinafter, embodiments of an OCT apparatus will be disclosed. The following chapters classified by < > may be used individually or in association with each other.

Schematic Configuration of OCT Apparatus

Figure 17:
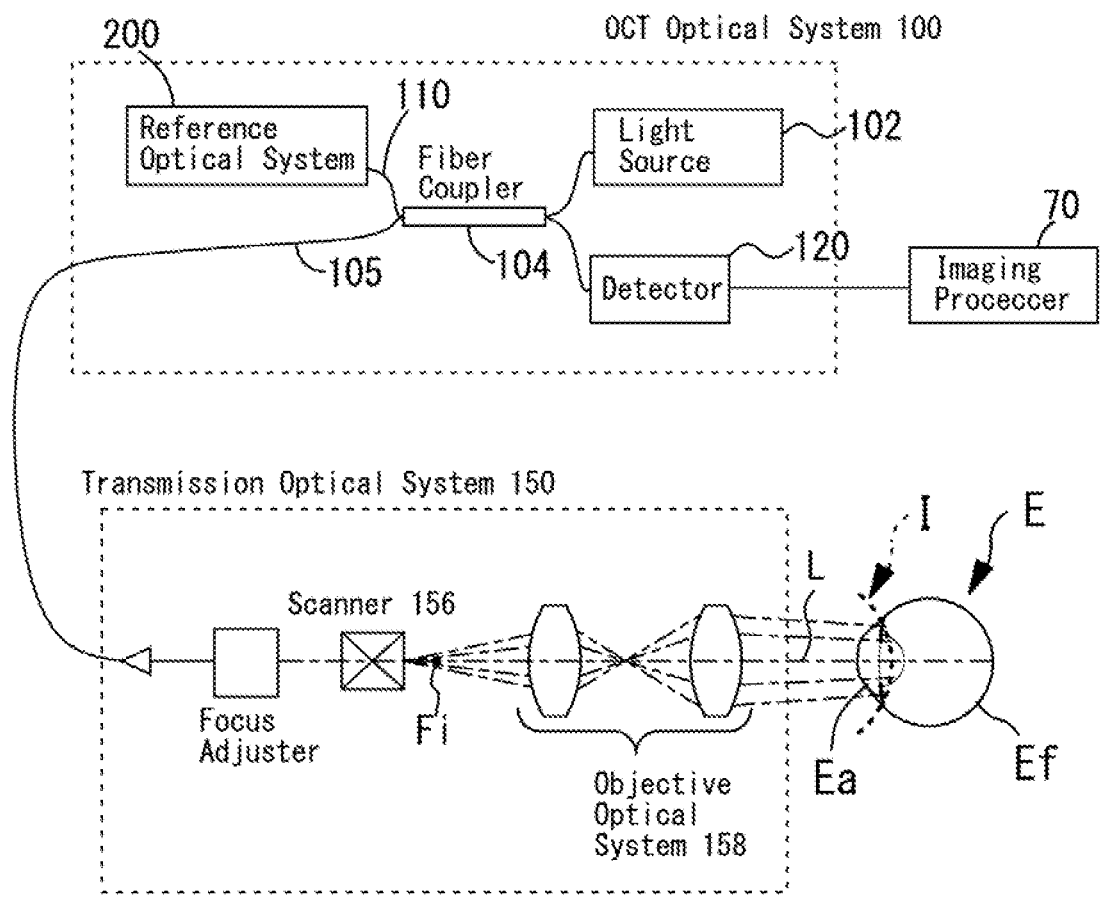
FIG. 17 is a diagram showing a schematic configuration of an OCT apparatus according to an embodiment.

FIG. 17 shows a schematic configuration of the OCT apparatus of the embodiment. The OCT apparatus of the embodiment includes at least an OCT optical system and an image processor. A spectral interference signal detected by the OCT optical system is processed by the image processor, and thereby OCT data of an examinee's eye is acquired. In addition, the OCT apparatus may further include an optical scanner and a light guiding optical system. The optical scanner and the light guiding optical system are disposed on a measurement optical path. In this case, the optical scanner may be a part of the light guiding optical system.

OCT Optical System

For example, the OCT optical system may be a Fourier-domain OCT optical system (an SS-OCT optical system or an SD-OCT optical system). The OCT optical system may include at least one of an optical splitter and a detector. The optical splitter splits light from an OCT light source into the measurement optical path and a reference optical path. The beam detector detects the spectral interference signal between measurement light guided to the examinee's eye through the measurement optical path and reference light from the reference optical path.

Image Processor

The image processor processes the spectral interference signal output from the OCT optical system so as to acquire OCT data of the examinee's eye. A function of the image processor may be performed by a control unit that manages overall operations of devices in the OCT apparatus, or the image processor may be an image processing device provided separately from the control unit. The image processor may generate various images such as a tomographic image (B-scan image), a three-dimensional image, and an OCT motion contrast image, based on OCT data.

Optical Scanner

The optical scanner is a device that deflects the measurement light from the optical splitter and performs scanning on tissue of the examinee's eye. It is preferable that the optical scanner performs two-dimensional scanning on the tissue with the measurement light. A plurality of optical scanners may be provided. In this case, a combination of two or more optical scanners that performs scanning in one direction with the measurement light may be provided. Specific examples of the optical scanner include a galvano mirror, a resonant mirror, a polygon mirror, an acousto-optic modulator, an MEMS scanner, or the like. In addition, an optical scanner having two degrees of freedom (a device capable of performing two-dimensional scanning as a single system) may be applied to the embodiment.

Light Guiding Optical System

The light guiding optical system includes an objective optical system and guides the measurement light from the optical splitter to the examinee's eye through the objective optical system. In addition, among scattering beams and reflected beams of the measurement light, a beam incident to the light guiding optical system is guided as a return beam to the detector of the OCT optical system.

The objective optical system is disposed between the optical scanner and the examinee's eye on the measurement optical path. In the embodiment, a concentrating plane (represented by a reference sign I in FIG. 17) of the measurement light having passed through the objective optical system is formed in an anterior chamber of the examinee's eye. That is, the concentrating plane of the measurement light from the optical scanner is formed in the anterior chamber of the examinee's eye by the light guiding optical system. In this case, the measurement light having passed through the objective optical system may be guided to the concentrating plane without intersecting an optical axis of the measurement optical path. For example, the light guiding optical system may have a concentrating position adjusting optical system such as a focusing lens. In this case, a position of the concentrating plane may be suitably adjusted by the concentrating position adjusting optical system such that the concentrating plane of the measurement light is set in the anterior chamber of the examinee's eye.

For example, a scanning range in a transverse direction of the anterior chamber, which is realized by the optical scanner and the objective optical system may be about a diameter of a cornea. More preferably, the scanning range may reach anterior chamber angles which are opposite to each other with an eye axis interposed therebetween.

In addition, the objective optical system may have a positive curve. That is, the concentrating plane of the measurement light, which is formed by the objective optical system, curves to have a convex shape on a side of the fundus. As shown in FIG. 17, the concentrating plane that is formed in the anterior chamber curves to be convex toward the side of the fundus, and thereby it is easy to image a crystalline lens with high resolution. Further, since a concentrating position is set at a shallow position with respect to a region of the crystalline lens on a side of peripheral portions such as an iris and a anterior chamber angle, a waste of beam intensity of the measurement light is suppressed. Consequently, it is easy to acquire a tomogram having high image quality or resolution in a wide range of the anterior chamber in a depth direction.

A curve of the objective optical system may be more preferably within a range in which a curvature radius (R) of the concentrating plane that is formed in the anterior chamber satisfies a relationship of R≤28.5 mm. The curvature of the concentrating plane (1/R) is represented by Expression (1).

$$\frac{1}{R} = \sum_{1}^{k} \frac{1}{n_k f_k} \quad (1)$$

Here, n represents a refractive index of each element (for example, a lens) that configures the objective optical system, and f represents a focal length of each element. In a case where a value on the right side is positive, the objective optical system has a positive curve. In addition, k, which is an index, corresponds to each lens.

The relationship of R≤28.5 mm is satisfied, and a curve is further added by the cornea. In this manner, it is possible to obtain a crystalline lens image and a anterior chamber angle image with high sensitivity. Since the cornea has a curved surface with a refractive index of about 1.377 and a curvature radius of about 7.8, as Expression (1), the cornea has an effect of adding a curvature represented by Expression (2).

$$1/nf=(n-1)/Nr=0.035 \qquad (2)$$

Incidentally, there is known anterior chamber OCT in the related art in which the light guiding optical system is a telecentric optical system, and the concentrating plane is a flat plane; however, a range in which it is possible to perform imaging at once in such an apparatus is about a range from a cornea surface to a crystalline lens front surface at most, and it is not possible to perform imaging in a range from the cornea surface to a crystalline lens rear surface. By contrast, in a case where the curvature radius (R) of the concentrating plane is set in a range of R≤28.5 mm as described above, it is possible to add a curve, which substantially equal to or larger than the curve obtained in the cornea, to the concentrating plane formed out of the cornea. As a result, it is easy to perform imaging at once in a range from the cornea surface to the crystalline lens rear surface.

In the embodiment, the objective optical system is a lens system formed by only one or a plurality of lenses. However, the objective optical system is not necessarily limited thereto and may be a mirror system formed only by one or a plurality of mirrors. In addition, the objective optical system may be obtained by combining the lens system and the mirror system.

Telecentricity of Measurement Light

The optical scanner may be disposed at a position separated from the objective optical system more than a focal point (focal point that is formed on a side of a light source and represented by a reference sign Fi in FIG. 17) of the objective optical system. As a result, a main ray of the measurement light emitted from the objective optical system to the examinee's eye may be inclined to an approaching direction toward the optical axis. The objective optical system has the positive curve, and thereby spectral interference signals in the cornea and a sclera are considered to have a decrease in sensitivity that toward the side of the peripheral portion. By contrast, the main ray of the measurement light that is emitted from the objective optical system toward the examinee's eye is inclined to the approaching direction toward the optical axis, and thereby it is easy to collect a return beam of the measurement light from the cornea, the sclera, or both thereof. In other words, a ratio of reflected or scattering beams out of the measurement optical path of the return beams from the cornea, the sclera, or both thereof decreases. As a result, it is possible to overcome a disadvantage of the positive curve of the objective optical system. That is, a tomogram, in which the cornea, the sclera, or both thereof, and the crystalline lens are well depicted, is acquired. In other words, a good tomogram is acquired in a wide range of the anterior chamber.

In addition, such disposition of the optical scanner means that an angle of view narrows as a deeper region is imaged; however, the disposition is rather convenient in a case where the anterior chamber is imaged to a deep region such as the crystalline lens rear surface. The number of A scans including the crystalline lens rear surface relatively increases without vignetting due to the iris or the like, and this leads to enhancing accuracy.

However, there is no need to dispose the optical scanner at the position separated from the objective optical system by a length longer than a focal length of the objective optical system. The optical scanner may be disposed at the focal point or may be disposed to be closer to the objective optical system than the focal point.

It is preferable that the optical scanner is disposed between a conjugated position with a pupil with respect to the objective optical system and an image-side focal point of the objective optical system. More preferably, a range of an angle of the main ray of the measurement light with respect to the optical axis is the following first angle or smaller. The first angle is defined by using a sphere having a cornea-equivalent radius and placed at an appropriate operation distance. That is, an angle formed between the optical axis and a first main ray as a main ray which matches one of normal lines of the sphere is the first angle. More preferably, a range of an angle of the main ray of the measurement light with respect to the optical axis is the following second angle or larger. The second angle is defined by using a sphere having a sclera-equivalent radius and placed at an appropriate operation distance. That is, an angle formed between the optical axis and a second main ray as a main ray which matches one of normal lines of the sphere is the second angle. The cornea-equivalent radius may be about 8 mm (to be more exact, 7.8 mm), and the sclera-equivalent radius may be about 14 mm. For example, a position of the appropriate operation distance is suitably set based on any one of the position of the concentrating plane of the OCT apparatus, a zero-delay position at which the reference optical path and the measurement optical path match each other, and the like.

Switching of Anterior Chamber Imaging Mode/Fundus Imaging Mode

As will be described with reference to FIGS. 16A and 16B, the OCT apparatus may further include a switching unit that switches a mode in the light guiding optical system in order to switch a depth position to be imaged. For example, the switching unit may switch an imaging mode between an anterior chamber imaging mode and a fundus imaging mode. The anterior chamber imaging mode is suitable for acquiring OCT data of the anterior chamber. The light guiding optical system in the anterior chamber imaging mode is configured as described above in the chapter of <Light Guiding Optical System>. That is, the concentrating plane of the measurement light is formed in the anterior chamber of the examinee's eye by the light guiding optical system at least in the anterior chamber imaging mode. On the other hand, the optical scanner and the pupil of the examinee's eye are disposed at conjugated positions in the fundus imaging mode. The optical scanner is disposed at the conjugated position with the pupil, and thereby the measurement light is turned around one point on the pupil in response to an operation of the optical scanner. Consequently, while the vignetting of the measurement light due to the iris is suppressed, it is possible to perform smooth scanning with the measurement light on the fundus.

For example, the switching unit may switch a mode of the light guiding optical system by any one of the following three methods.

(1) Method 1: Change a positional relationship between the focal point of the objective optical system and the optical scanner
(2) Method 2: Insert or remove a lens into and from the objective optical system
(3) Method 3: Combine both Method 1 and Method 2

It is needless to say that the methods are provided only as examples, and thus mode switching of the light guiding optical system may be realized by another method.

It is preferable that the concentrating plane of the measurement light curves along the fundus curve in the fundus imaging mode. That is, it is preferable that the objective optical system has a positive curve even in the fundus imaging mode such that the curve of the concentrating plane of the measurement light is maintained to have the convex shape. Consequently, it is easy to acquire a tomogram of the fundus with high resolution and image quality in each of a center portion and a peripheral portion.

In a case where the switching unit changes the positional relationship between the focal point of the objective optical system and the optical scanner, thereby switching the depth position to be imaged, a curvature value (Petzval sum) of curves on the objective optical system does not change before and after the switching, and thus the curve of the concentrating plane of the measurement light can be naturally curved toward the side of the fundus even during fundus imaging.

Currently, among commercially available OCT for fundus, even an apparatus having a wide angle of view (for example, a product name of "PLEX Elite 9000" manufactured by Carl Zeiss Co. Ltd.) obtains a range in which the fundus is in an angle of view of about 16 mm and a depth is about 3 mm (in terms of air).

In this case, a curvature radius of a curve necessary for fundus imaging is calculated as a value of Expression (3) from computing of a sag amount.

$$\frac{8^2 + 3^2}{2 \times 3} = 12.167 \quad (3)$$

The value is obtained by considering an influence of a curve formed by the cornea. In this respect, the curve by the cornea is subtracted as described in Expression (4), and thereby it is possible to obtain a desirable curve of the concentrating plane in the OCT apparatus that is capable of switching between the anterior chamber imaging and the fundus imaging.

$$\frac{1}{12.167} = \frac{1}{R} + \frac{1.337 - 1}{1.337 \times 7.8} \quad (4)$$

As a result, it is preferable to have R=21.2354 as the curve of the concentrating plane by the objective optical system. That is, it is preferable to have a range of R≤21.

Plurality of Reference Optical Paths

In addition, the OCT apparatus in the embodiment may have the following configuration.

For example, the OCT optical system may be provided with a plurality of reference optical paths. For example, the OCT optical system may be provided with a first reference optical path and a second reference optical path which are set to have different optical path lengths from each other. In this case, one of the first reference optical path and the second reference optical path may be set to have a optical path length for obtaining OCT data including the cornea (for example, the cornea and the crystalline lens front surface) of the examinee's eye, and the other of the first reference optical path and the second reference optical path may be set to have an optical path length for obtaining OCT data including the crystalline lens (for example, the crystalline lens rear surface) of the examinee's eye. In addition, one of the first reference optical path and the second reference optical path may be set to have an optical path length for obtaining OCT data including the anterior chamber (for example, the cornea and the crystalline lens) of the examinee's eye, and the other of the first reference optical path and the second reference optical path may be set to have an optical path length for obtaining OCT data including the fundus.

In addition, a coupler that couples the return beam of the measurement light with the reference light may be further provided for each reference optical path, and thereby it is possible to simultaneously acquire interference signals corresponding to different depth regions from each other and, as a result, to acquire OCT data in a wide range of the examination target eye with high intensity.

Optical Path Length Difference Adjustment in Response to Switching of Imaging Mode In addition, the OCT apparatus may further include an adjusting unit that adjusts an optical path length difference (OPL) between the measurement optical path and the reference optical path in response to the mode switching by the switching unit. For example, it may be necessary to adjust the OPL depending on a depth region in which the OCT data is acquired. The adjusting unit adjusts at least one of an optical path length of the reference optical path and an optical path length from a splitting unit to the objective optical system of the measurement optical path. The adjusting unit may be controlled by the control unit of the OCT apparatus. The control unit may execute a switching operation of controlling the adjusting unit so as to switch the optical path length, thereby, offsetting at least a part of a change in OPL, which occurs before and after the mode switching.

Altered Embodiment: To Switch Imaging Position by Attaching and Detaching Attachment Optical System An attachment optical system (refer to FIG. 18) may be used in the switching unit that is used for switching the mode of the light guiding optical system between the anterior chamber imaging mode and the fundus imaging mode. The attachment optical system is attached to and detached from a housing surface of the apparatus.

Incidentally, there is known a technology in the related art, in which an attachment optical system is installed in an apparatus having an optical system applied to acquire OCT data of the fundus, thereby, switching the system to the optical system applied to anterior chamber imaging (for example, see "JP-A-2011-147612").

By contrast, an altered embodiment provides the description of new switching means and a new optical system, in which the attachment optical system is not installed, and thereby the anterior chamber imaging mode is set, and the attachment optical system is installed, and thereby the fundus imaging mode is set. The attachment optical system is inserted and removed (for example, attached and detached) between the objective optical system and the examinee's eye on the measurement optical path thereof.

The objective optical system guides the measurement light having passed through the optical scanner to a first concentrating plane without causing the measurement light to intersect the optical axis of the measurement optical path. In this case, the objective optical system causes the measurement light to be concentrated on the first concentrating plane. For example, the objective optical system may be the telecentric optical system. In this case, the focal point of the objective optical system substantially matches a turning position of the measurement light by the optical scanner, and thereby a beam flux having passed through the objective optical system is emitted as a telecentric beam flux toward the side of the examinee's eye. Here, the "telecentric beam flux" is not limited to a beam flux having a main ray that is completely parallel to the optical axis and may be a beam flux having a main ray that is inclined with respect to the optical axis.

The objective optical system has positive power (refractive power) overall. Consequently, the measurement light having passed through the objective optical system is concentrated (converges) on a flat plane or a curved plane that intersects the optical axis. The flat plane or the curved plane is the first concentrating plane. It is preferable to set an operation distance (distance from an end portion of the apparatus to the cornea) Wd when the OCT data of the anterior chamber is obtained, based on a position of the first concentrating plane. That is, in a case where the examinee's eye is positioned in an overlap range or in the vicinity of the first concentrating plane, the OCT data of the anterior chamber is smoothly obtained. In this respect, it is desirable to set the operation distance in a positional relationship between the examinee's eye and the apparatus in this case.

In the altered embodiment, the OCT optical system, the optical scanner, and the objective optical system belong to an apparatus main body of the OCT apparatus. The units may be accommodated in a housing of the apparatus main body. The housing may be provided with an inspection window on a side surface on the side of the examinee's eye.

Attachment Optical System

In the altered embodiment, the attachment optical system may be insertable and removable between the objective optical system and the examinee's eye on the measurement optical path. The attachment optical system may be provided separately from the apparatus main body of the OCT apparatus. In this case, the attachment optical system is attached and detached through the inspection window of the housing in the apparatus main body, thereby being inserted and removed on the measurement optical path. The attachment optical system may be completely separable from the apparatus main body of the OCT apparatus. In addition, a lens tube of the attachment optical system may be attached in advance to the apparatus main body of the OCT apparatus with a hinge or the like, or the attachment optical system may be rotated by the hinge, and thereby the attachment optical system is capable of being attached and detached with respect to the inspection window.

The attachment optical system is inserted on the measurement optical path, and thereby the measurement light from the objective optical system is bent toward the side of the optical path. Consequently, the turning point of the measurement light is formed at a conjugated position with the optical scanner with respect to the objective optical system and the attachment optical system. In addition, the measurement light having passed the turning point is concentrated on a second concentrating plane. It is preferable to set the operation distance when the OCT data of the fundus is obtained, based on a position of the turning point. That is, in a case where a position of the anterior chamber (more preferably, the pupil) matches the turning point, it is easy for the measurement light to reach the fundus without vignetting due to the iris. Hence, the operation distance may be set in a positional relationship between the examinee's eye and the apparatus in a case where the anterior chamber (more preferably, the pupil) matches the turning point. In addition, it is preferable that the second concentrating plane is formed in the vicinity of the fundus.

As described above, the OCT apparatus in the altered embodiment is capable of switching an acquisition range of the OCT data by a new switching method in which the attachment optical system is inserted into and removed from the optical system applied to acquire the OCT data in the anterior chamber, and thereby the system is switched to the optical system applied to acquire the OCT data in the fundus.

Here, in an optical system in the related art as disclosed in "JP-A-2016-123467", a pupil image is relayed by the attachment optical system. To be more specific, the attachment optical system generates a Fourier-transformed image of the pupil once, and then Fourier transform is again performed such that the beam returns to the pupil again. As a result, the attachment optical system is likely to increase in size. Thus, when the optical system is designed to have large power in order to reduce a size of the optical system, a problem arises in that an aberration that influences the OCT data is likely to occur in each unit.

In the OCT apparatus according to the altered embodiment, the optical system between the optical splitter and the objective optical system generates the Fourier-transformed image of the pupil in advance. Hence, the attachment optical system only needs to convert the Fourier-transformed image into a pupil image, that is, it is possible to perform the Fourier transform of the pupil and the image once by the attachment optical system. Hence, it is easy for the attachment optical system to have a compact configuration. As a result, while expected power is obtained, it is easy to suppress the aberration. Therefore, according to the OCT apparatus in the altered embodiment, it is easy to achieve design in which the acquisition range of the OCT data in the fundus is wide, when the attachment optical system is inserted. For example, it is possible to realize the OCT apparatus having a scanning range at an angle of $\phi 80°$ or larger in the fundus (here, the "scanning range" means a size of the angle of view that depends on the optical system disposed to be closer to the side of the examinee's eye than the optical scanner.

In addition, the attachment optical system may bend the beam flux toward the side of the optical axis such that a first solid angle indicating a scanning range of the measurement light in the vicinity of the optical scanner is smaller than a second solid angle indicating a scanning range of the measurement light in the vicinity of the turning point, for example.

The attachment optical system may be a refraction system (lens system), may be a reflection system (mirror system), or may be a combination of both of the systems.

Refractive Attachment Optical System

Here, a detailed configuration in a case where the attachment optical system is a lens attachment (that is, a refractive attachment optical system) as an example is described. In this case, the attachment optical system includes one or more lenses.

The attachment optical system may have two types of lens groups of a first lens group and a second lens group. In this case, the first lens group and the second lens group are disposed to be arranged in this order from the objective optical system toward the examinee's eye. It is preferable that the first lens group has negative power, and the second lens group has the positive power. In this case, since the maximum ray height of the measurement light in the attachment optical system is obtained at a position closer to the examinee's eye, it is easy to secure a longer operation distance. For example, this is true of back focus magnification in a retrofocus optical system described in U.S. Pat. No. 4,867,555.

Lenses included in the attachment optical system may be all spherical lenses. It is needless to say that some or all of the lenses may be aspherical lenses.

Reduction in Aberration by Aberration Correcting Lens of Attachment Optical System The attachment optical system may include an aberration correcting lens. The aberration correcting lens may suppress an occurrence of an aberration by the attachment optical system, the aberration significantly influencing the OCT data in the fundus. It is possible to provide, as an example of an aberration that significantly influences the OCT data in the fundus, asymmetrical aberration such as a coma or astigmatism and a curved field. In addition, the aberration correcting lens may have a component having the curved field for causing a shape (mainly, a curvature) of the concentrating plane (second concentrating plane) formed by the measurement light having passed through the attachment optical system to resemble a curved surface of the fundus. In other words, the aberration correcting lens may have a component having the curved field with consideration for a curve in the surface of the fundus. Deviation between the second concentrating plane and the fundus surface increases as it is closer to the peripheral portion, and thus image forming is degraded. This is likely to result in a problem in widening the scanning range. By contrast, the aberration correcting lens may have a component having the curved field for resembling the shape (mainly, the curvature) of the concentrating plane (second concentrating plane) formed by the measurement light having passed through the attachment optical system, it is possible to suppress the deviation, and thus it is easy to smoothly obtain the OCT data in a wide range of the fundus.

The aberration correcting lens may be included in the first lens group or in the second lens group. In addition, the aberration correcting lens may be disposed at least one by one in each of the first lens group and the second lens group.

The aberration correcting lens may be a compound lens. The compound lens is obtained by bonding a lens having negative power (concave lens) and a lens having positive power (convex lens). In a case where each of the lens in the first lens group and the second lens group is the spherical lens, the compound lens is effective to suppress the above-exemplified aberration.

The operation distance Wd (operation distance when the OCT data of the anterior chamber is obtained) in an uninstalled state of the attachment optical system is set such that the lenses are disposed in a positional relationship in which a concentrating point of the measurement light does not match a surface of the lens.

In a case where the compound lens is included in the first lens group, a range of a distance (Wd) from the objective optical system to a first compound lens is determined by Expression (5); however, it is preferable to reduce an influence of reflection due to a lens surface.

$$Z < Wd < Z + D \quad (5)$$

Here, Z represents a distance from an optical surface (for example, a lens surface) that is positioned to be closest to the side of the examinee's eye in the objective optical system to a lens surface positioned closest to the side of the objective optical system in the first compound lens. D represents a thickness of the first compound lens on an optical axis L.

In a case where the compound lens is provided in the second lens group, the second lens group may further have a lens that bends the measurement light toward the optical axis at a position, at which the maximum ray height is obtained with respect to the optical axis, separately from the compound lens. The lens may have principal positive power in the attachment optical system. The lens that plays a role of reducing the aberration is separately provided from the lens that plays a role of bending the ray toward the side of the optical axis, and thereby it is easy to realize high image forming performance at an expected angle of view. It is needless to say that an aspherical lens may be used for correcting the aberration even when the lens has the principal positive power. In addition, it is preferable that the lens that bends the measurement light toward the optical axis is disposed closer to the side of the examinee's eye than the compound lens. That is, since the maximum ray height of the measurement light is obtained at a position closer to the examinee's eye, it is easy to secure a longer operation distance.

The compound lens may have a configuration in which the lens front surface and the lens rear surface have a meniscus shape of a convex shape toward the side of the examinee's eye. The compound lens has the meniscus shape, thereby, being similar to a concentric configuration, and thus an occurrence of the asymmetrical aberration such as a coma or astigmatism is suppressed.

In a case where the compound lens is provided in the second lens group, the lens having the negative power in the compound lens may be formed of a material having a lower refractive index than the lens having the positive power. Consequently, the measurement light is significantly refracted toward the optical axis by the second lens group, and thereby an occurrence of the curved field is reduced. In this case, when the compound lens is further also provided in the first lens group, the lens having the negative power in the compound lens of the first lens group may be formed of a material having a higher refractive index than the lens having the positive power. As described above, in a case where the compound lens is provided in each of the first lens group and the second group, of the lens having the negative power and the lens having the positive power in the compound lens, lenses having a higher scattering property may be different from each other between the first lens group and the second lens group. Consequently, since at least a part of the curved field occurring in the compound lenses is offset, such a configuration is advantageous in a case of suppressing the curved field occurring in the attachment optical system.

In a case where a total of two compound lens lenses are provided one by one in both the first lens group and the second lens group, it is preferable that an aberration suppressing effect is more weighted on the curved field than a chromatic aberration. In this case, a condition that the two compound lenses need to satisfy is represented by Expression (6).

$$\frac{N_{1p}f_{1p} + N_{1n}f_{1n}}{N_{2p}f_{2p} + N_{2n}f_{2n}} > \frac{N_{1p}N_{1n}|f_{1p} + f_{1n}|}{N_{2p}N_{2n}|f_{2p} + f_{2n}|} \quad (6)$$

Here, N represents a refractive index of a lens, and f represents a focal length of a lens. 1p as an index represents a value of a lens having the positive power in the compound lens in the first lens group, In represents a value of a lens having the negative power in the same compound lens, 2p represents a value of a lens having the positive power in the compound lens in the second lens group, and 2n represents a value of a lens having the negative power in the same compound lens.

In the field of ophthalmology, there is known an apparatus having a configuration in which an imaging device such as a fundus camera or an SLO that images a front image of the fundus is integrally provided in the OCT apparatus. In this type of apparatus, the objective optical system is shared by an optical system (front-side imaging optical system) for imaging the front image and the OCT apparatus. In this case, the attachment optical system is also considered to be shared. In this case, the aberration suppressing effect of the two compound lenses in the attachment optical system may be more weighted on the chromatic aberration than the curved field. For example, in a case where color imaging is performed in the front-side imaging optical system, an influence of the chromatic aberration decreases.

EXAMPLES

Figure 1:
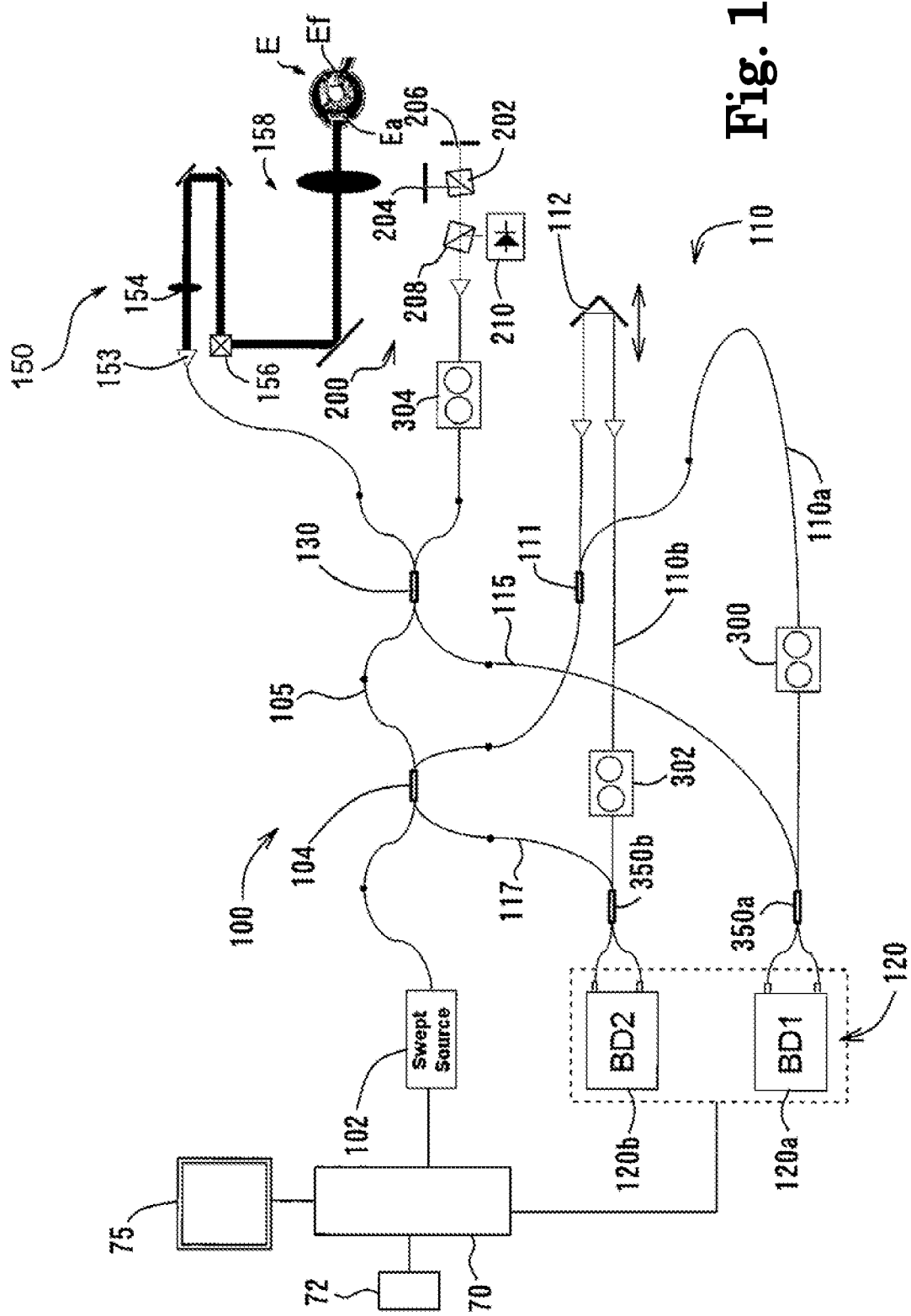
FIG. 1 is a diagram showing an example of an OCT apparatus according to the example.

In the present example, an optical coherence tomography (OCT) apparatus illustrated in FIG. 1 is used as the OCT apparatus. The OCT apparatus according to the present example basically includes, for example, a wavelength sweep type OCT (SS-OCT: swept source-OCT), and for example, includes a wavelength variable light source 102, an interference optical system (OCT optical system) 100, an arithmetic controller (arithmetic control section) 70. In addition, the OCT apparatus may be provided with a memory 72, a display section 75, a front image observation system (not illustrated) and a fixation target projection system. The arithmetic controller (hereinafter, control section) 70 is connected to the wavelength variable light source 102, the interference optical system 100, the memory 72, and the display section 75.

The interference optical system 100 guides the measurement light to an eye E by a light guiding optical system 150. The interference optical system 100 guides the reference light to a reference optical system 110. The interference optical system 100 causes a detector (light receiving element) 120 to receive the interference signal light acquired by the interference between the measurement light reflected by the eye E and the reference light. Furthermore, the interference optical system 100 of the present example includes an FPN generation optical system 200 (will be described in detail later). In addition, the interference optical system 100 is mounted in a housing (apparatus main body) which is not illustrated, and the housing is moved three-dimensionally with respect to the eye E by a well-known alignment movement mechanism via an operation member, such as a joystick, and accordingly, alignment with respect to the examinee's eye may be performed.

An SS-OCT method is used for the interference optical system 100, and the wavelength variable light source (wavelength scanning type light source) which changes the emitted wavelength at a high speed in time is used as the light source 102. The light source 102 is configured with, for example, a laser medium, a resonator, and a wavelength selection filter. In addition, examples of the wavelength selection filter include a combination of a diffraction grating and a polygon mirror, and a filter using a Fabry-Perot etalon.

In addition, as the light source 102, a VCSEL type wavelength variable light source may be used.

A coupler (splitter) 104 is used as the first optical splitter and splits the light emitted from the light source 102 into the measurement optical path and the reference optical path. For example, the coupler 104 guides the light from the light source 102 to an optical fiber 105 on the measurement optical path side and guides the light to the reference optical system 110 on the reference optical path side.

A coupler (splitter) 130 is used as the second optical splitter and splits the light (measurement light) from the optical fiber 105 into the optical path of the light guiding optical system 150 and the optical path of the FPN generation optical system 200. In other words, in the measurement optical path, the light guiding optical system 150 and the FPN generation optical system 200 are provided. The coupler (splitter) 130 may be an optical splitter or a circulator.

Light Guiding Optical System

The light guiding optical system 150 is provided to guide the measurement light to the eye E. In the light guiding optical system 150, for example, an optical fiber 152, a coupler 153, a collimator lens 154, an optical scanner 156, and an objective lens system 158 may be sequentially provided. In this case, the measurement light becomes a parallel beam by the collimator lens 154 through the optical fiber 152 and the coupler 153, and is directed toward the optical scanner 156. The eye E is irradiated with the light passing through the optical scanner 156 through the objective lens system 158. Both the anterior ocular segment and the posterior ocular segment are irradiated with the measurement light, and is scattered or reflected by each tissue.

The optical scanner 156 may cause the measurement light to scan in the X and Y directions (transverse direction) on the eye E. The optical scanner 156 is, for example, two Galvano mirrors, and a reflection angle thereof is voluntarily adjusted by a driving mechanism. The luminous flux emitted from the light source 102 has the reflection (traveling) direction changed, and is scanned in any direction on the fundus. As the optical scanner 156, for example, an acousto-optical modulator (AOM) or the like for changing the traveling (deflection) direction of light may be used in addition to the reflecting mirror (Galvano mirror, polygon mirror, or resonant scanner).

In this case, the scattering light (reflected light) from the eye E by the measurement light passes through the objective lens system 158, the optical scanner 156, the collimator lens 154, the coupler 153, and the optical fiber 152, and then reaches the coupler 130. The coupler 130 splits the light from the optical fiber 152 into an optical path (for example, an optical fiber 115 to a coupler 350a) toward a first detector 120a and an optical path (for example, the optical fiber 105, the coupler 104, and an optical fiber 117 to a coupler 350b) toward a second detector 120b.

In the measurement light split by the coupler 130, the measurement light that has passed through the optical path toward the first detector 120a is combined with the reference light from a first reference optical path 110a by the coupler 350a to interfere. In addition, the measurement light that has passed through the optical path toward the second detector 120b is combined with the reference light from a second reference optical path 110b by the coupler 350b to interfere.

Reference Optical System

The reference optical system 110 generates the reference light combined with the reflected light acquired by the reflection of the measurement light in the eye E. The reference light that has passed through the reference optical system 110 is combined with the light from the measurement optical path by the coupler (for example, the couplers 350*a* and 350*b*) to interfere. The reference optical system 110 may be a Michelson type or a Mach-Zehnder type.

The reference optical system 110 may be formed, for example, by a reflection optical system and may guide the light from the coupler 104 to the detector 120 by reflecting the light with the reflection optical system. The reference optical system 110 may be formed by a transmission optical system. In this case, the reference optical system 110 guides the light to the detector 120 by transmitting the light from the coupler 104 without returning the light.

In addition, an optical member for adjusting the optical path length difference between the measurement light and the reference light may be disposed in at least one of the measurement optical path and the reference optical path. For example, by integrally moving the collimator lens 154 and the coupler 153, the optical path length of the measurement light may be adjusted, and as a result, the optical path length difference between the measurement light and the reference light may be adjusted. Naturally, the optical member disposed in the reference optical path is moved, and as a result, the optical path length difference between the measurement light and the reference light may be adjusted.

In the present example, a plurality of reference optical paths may be provided as the reference optical system 110, and for example, the first reference optical path 110*a* and the second reference optical path 110*b* may be provided.

The reference optical system 110 may be provided with, for example, an optical splitter (for example, a coupler 111) for splitting the reference optical path into the first reference optical path 110*a* and the second reference optical path 110*b*. For at least one of the first reference optical path 110*a* and the second reference optical path 110*b*, for example, an optical member 112 which is moved to change the optical path length of the reference light may be provided. The optical member 112 may be moved by a driving section (not illustrated) controlled by the control section 70.

For example, the reference light from the coupler 104 is split by the coupler 111 into the first reference optical path 110*a* and the second reference optical path 110*b*. The reference light that has passed through the first reference optical path 110*a* is combined with the measurement light from the optical fiber 115 by the coupler 350*a* to interfere. The reference light that has passed through the second reference optical path 110*b* is combined with the measurement light from the optical fiber 117 by the coupler 350*b* to interfere.

The first reference optical path 110*a* and the second reference optical path 110*b* may be set to have optical path lengths different from each other. According to this, for example, interference signals that correspond to depth regions different from each other can be acquired at the same time, and as a result, a wide-range of OCT data can be simultaneously acquired.

For example, the first reference optical path 110*a* may be provided to obtain an interference signal that corresponds to a first depth region (for example, the crystalline lens and the fundus) in the examinee's eye, and the second reference optical path 110*b* may be provided to obtain an interference signal that corresponds to a second depth region (for example, the cornea) in the examinee's eye. In this case, the second depth region is set to a region different from the first depth region. In this case, the first depth region and the second depth region may be regions separated from each other, may regions adjacent to each other, or may be regions which overlap each other.

In addition, the first reference optical path 110*a* and the second reference optical path 110*b* may be set to have the same optical path lengths. According to this, for example, interference signals that correspond to the same depth region can be acquired at the same time, and as a result, the plurality of OCT data related to the same region can be simultaneously acquired.

Photodetector

The detector 120 is provided for detecting interference by the light from the measurement optical path and the light from the reference optical path. In addition, the detector 120 may be a light receiving element, for example, a point sensor including only one light receiving portion, and for example, an avalanche photo diode may be used.

In the present example, as the detector 120, the first detector 120*a* and the second detector 120*b* different from the first detector 120*a* may be provided. The first detector 120*a* may be provided as a detector for detecting the first interference signal between the reference light from the first reference optical path 110*a* and the measurement light from the optical fiber 115. The second detector 120*b* may be provided as a detector for detecting the second interference signal between the reference light from the second reference optical path 110*b* and the measurement light from the optical fiber 117. In this case, by detecting the first interference signal with the first detector 120*a* and at the same time detecting the second interference signal with the second detector 120*b*, the first interference signal and the second interference signal can be simultaneously detected.

In addition, the first detector 120*a* and the second detector 120*b* may be balanced detectors, respectively. In this case, each of the first detector 120*a* and the second detector 120*b* includes a plurality of light receiving elements, obtains the difference between the interference signal from the first light receiving element and the interference signal from the second light receiving element, and can reduce unnecessary noise included in the interference signal.

FPN Generation Optical System

The FPN generation optical system 200 may be provided to generate the FPN signal. The FPN generation optical system 200 may include at least one optical member (for example, a first optical member 204 or a second optical member 206) for generating the FPN. In the present example, the FPN generation optical system 200 is disposed at a position branched from the optical path in which the measurement light is directed toward the examinee's eye.

As the FPN generation optical system 200, for example, the reflection optical system may be used, and for example, as the FPN generation optical member, for example, a light reflecting member (for example, a mirror) may be used. In addition, in the present example, a plurality of optical members for generating the FPN are provided, but the invention is not limited thereto, and the FPN generation optical system 200 may be configured to have one optical member for generating the FPN.

The FPN signal is detected by the first detector 120*a* together with the first interference signal, and the FPN signal is detected by the second detector 120*b* together with the second interference signal. The FPN signal includes, for example, a composition of the first OCT data based on the first interference signal and the second OCT data based on the second interference signal (which will be described in detail later), wavenumber mapping correction of each of the interference signals, polarization adjustment and the like may be used.

For example, the FPN generation optical system 200 may be provided to generate a first FPN signal and a second FPN signal. For example, the FPN generation optical system 200 may include at least the first optical member 204 for generating the first FPN or the second optical member 206 for generating the second FPN. The second optical member 206 may be disposed such that the light that has passed through the second optical member has an optical path length different from the optical path length due to the light that has passed through the first optical member 204. According to this, the second FPN is generated at a position different from that of the first FPN. In addition, the zero delay position which will be described later corresponds to the position at which the optical path length of the measurement light is identical to the optical path length of the reference light on the OCT data.

By using the first optical member 204 and the second optical member 206 at the same time, it is possible to simultaneously generate two FPN signals, and according to this, it is possible to reduce the influence of the time shift when processing the two FPN signals. In addition, the FPN optical system 200 may include three or more FPN generation optical members, and by using the members at the same time, it is possible to simultaneously generate three or more FPN signals.

As the FPN generation optical system 200, for example, the reflection optical system may be used, and for example, as the FPN generation optical member, for example, a light reflecting member (for example, a mirror) may be used. In the present example, mirrors are used as the first FPN generation optical member 204 and the second FPN generation optical member 206, but the invention is not limited thereto.

In this case, after the light from the coupler 130 passes through the first optical member 204 or the second optical member 206, the light returns to the coupler 130, passes through the path similar to the light from the light guiding optical system 150, and reaches the coupler 350a and the coupler 350b. The light from the FPN generation optical system 200 is combined with the reference light at the couplers 350a and 350b to interfere. In addition, the optical path length from the light source 102 and the FPN generation optical system 200 to the couplers 350a and 350b, and the optical path length from the light source 102 and the reference optical system 110 to the couplers 350a and 350b may be set to substantially the same length.

For example, as the light that has passed through the first optical member 204 interferes with the reference light, the interference signal light that corresponds to the first FPN is generated, the first FPN signal is generated in the detector 120, the light that has passed through the second optical member 206 interferes with the reference light, and accordingly, the interference signal light that corresponds to the second FPN is generated, and the second FPN signal is generated in the detector 120. As a result, for example, both the first FPN signal and the second FPN signal are simultaneously detected by the detector 120.

In a case where the FPN signal is used in predetermined processing, in each of the detector 120a and the detector 120b, both of the first FPN signal and the second FPN signal may be simultaneously detected, one FPN signal may be detected by the detector 120a, and the other FPN signal may be detected and by the detector 120b. In addition, both the first FPN signal and the second FPN signal are simultaneously detected in one of the detector 120a and the detector 120b, and one of the first FPN signal and the second FPN signal may be detected in the other of the detector 120a and the detector 120b. In addition, at least one FPN signal is detected in one of the detector 120a and the detector 120b, and the FPN signal may not be detected in the other of the detector 120a and the detector 120b.

In addition, a light amount monitor 210 may be disposed in the FPN generation optical system 200, and the light from the light source 102 is detected by the light amount monitor 120 through an optical splitter 208. An output signal from the light amount monitor 120 may be used for determining whether or not the amount of emitted light of the light source 102 is appropriate.

Light Amount Branching Ratio

Here, the coupler 130 splits the light from the coupler 104 into the optical path of the light guiding optical system 150 and the optical path of the FPN generation optical system 200, and also splits the light from the light guiding optical system 150 and the FPN generation optical system 200 into the optical path (for example, optical fiber 115 to coupler 350a) toward the first detector 350a and the optical path toward the coupler 104 (for example, the optical fiber 105, the coupler 104, and the optical fiber 117 to the coupler 350b).

A light amount split ratio S1 of the coupler 130 when splitting the light from the fiber 105 may be set such that more amount of light is guided to the FPN generation optical system 200 than the light guiding optical system 150. In this case, the light amount ratio at which the light from the fiber 105 is split by a coupler 130 is smaller in the light guiding optical system 150 that in the FPN generation optical system 200.

A light amount split ratio S2 of the coupler 130 when splitting the light from the light guiding optical system 150 depends on the light amount split ratio S1. As a result, regarding the light from the light guiding optical system 150, more amount of light is guided to the optical path toward the second detector 120a than the optical path toward the first detector 120a. In this case, the light amount ratio at which the light from the light guiding optical system 150 is split by the coupler 130 is smaller in the optical path toward the first detector 120a than in the optical path toward the coupler 104.

The measurement light that has passed through the optical path toward the first detector 120a interferes with the light from the first reference optical path 110a and then is detected as the first interference signal by the first detector 120a. Meanwhile, the measurement light toward the coupler 104 is split by the coupler 104 into the optical path toward the light source 102 and the optical path (for example, the optical fiber 117 to the coupler 350b) toward the second detector 120b. A light amount split ratio S4 when splitting the light from the coupler 130 depends on the light amount split ratio S3 when splitting the light from the light source 102 into the measurement optical path and the reference optical path. In a case where the light amount split ratio S3 is set such that more amount of light is guided to the reference optical path than that in the measurement optical path, the light amount ratio at which the light from the coupler 130 is split by the coupler 104 is smaller in the optical path toward the light source 102 than in the optical path toward the second detector 120b. As a result, regarding the light from the coupler 130, more amount of light is guided to the optical path toward the second detector 120b than the optical path toward the light source 102. The measurement light that has passed through the optical path toward the second detector 120b interferes with the light from the second reference optical path 110b and then is detected as the second interference signal by the second detector 120b.

To summarize the above-described configuration, the light amount split ratio S2 of the coupler 130 is set to be smaller in the optical path toward the first detector 120a than in the optical path toward the coupler 104, and the light amount split ratio S4 of the coupler 104 is set to be smaller in the optical path toward the light source 102 than in the optical path toward the second detector 120b.

As a result, it is possible to detect the first interference signal detected by the first detector 120a and the second interference signal detected by the second detector 120b with an appropriate balance. In other words, in a case of the optical path toward the second detector 120b through the coupler 104, the light from the light guiding optical system 150 passes through the plurality of optical splitters (for example, the coupler 130 and the coupler 104), and thus, the number of times of attenuation of the light amount is large. Meanwhile, in a case of the optical path toward the first detector 120a, the light from the light guiding optical system 150 reaches the first detector 120a through the coupler 130, and thus, the number of times of attenuation of the light amount is relatively small.

Here, the light amount split ratio S2 of the coupler 130 is smaller in the optical path toward the first detector 120a than in the optical path toward the coupler 104, and the light amount split ratio S4 of the coupler 104 is smaller in the optical path toward the light source 102 than in the optical path toward the second detector 120b, and accordingly, it is possible to reduce the attenuation of the light amount even when the attenuation of the light amount is performed plural times, and as a result, it is possible to reduce the difference in signal intensity between the first detector 120a and the second detector 120b. Therefore, the difference in signal intensity between the OCT data obtained by the first detector 120a and the OCT data obtained by the second detector 120b is reduced, and appropriate OCT data can be acquired, respectively.

In addition, the light amount split ratio S2 of the coupler 130 and the light amount split ratio S4 of the coupler 104 may be set such that the light amount ratios of the optical path toward the first detector 120a and the optical path toward the second detector 120b are the same as each other. As an example, the light amount split ratio S2 of the coupler 130 may be set such that the optical path toward the first detector 120a: the optical path toward the coupler 104=6:4, and the light amount split ratio S4 of the coupler 102 may be set such that the optical path toward the light source 102: the optical path toward the second detector 120b=1:2.

Not being limited to the description above, with respect to the light amount split ratio S2 of the coupler 130 and the light amount split ratio S4 of the coupler 104, taking into consideration the difference in amount of reflected light at the capturing part of the OCT data detected by the first detector 120a and the second detector 120b, the light amount split ratio may be set. In other words, the reflected light from the cornea of the examinee's eye has a large amount of reflected light, but the light from the crystalline lens and the fundus has a relatively small amount of reflected light. Here, in consideration of the ratio of the amount of the reflected light depending on the capturing part, as a result, the light amount split ratio S2 of the coupler 130 and the light amount split ratio S4 of the coupler 104 may be set such that the signal intensity of the OCT data between the first detector 120a and the second detector 120b are the same.

In addition, in the present example, when the light from the light guiding optical system 150 is guided to the plurality of detectors, the light is divided into the light toward the first detector 120a through one optical splitter (for example, the coupler 130) and the light toward the second detector 120b through the plurality of couplers (for example, the coupler 130 and the coupler 104) because the light from the light guiding optical system 150 is more efficiently guided to each of the detectors. Such an optical disposition is particularly advantageous in a case where the amount of emitted light of the light source 120 is limited and the reflected light from the examinee's eye is weak.

Figure 2:
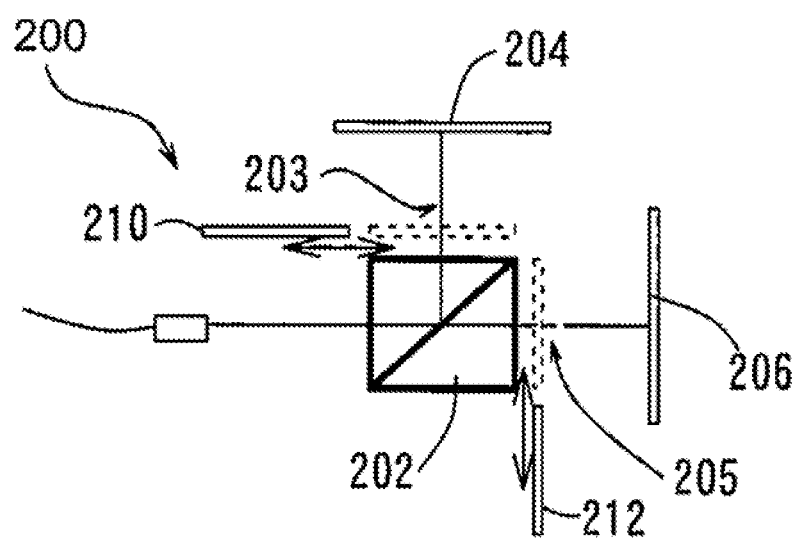
FIG. 2 is a diagram showing an example of an FPN generating optical system according to the example.

FIG. 2 is a view illustrating an example of an FPN generation optical system according to the present example. The FPN generation optical system 200 may include, for example, at least a first optical path 203 including the first optical member 204 and a second optical path 205 including the second optical member 206. Here, between the first optical path 203 and the second optical path 205, by making the optical path length of the first optical path 203 and the optical path length of the second optical path 205 different from each other, the second FPN is generated at a position different from that of the first FPN. For example, by making the optical path length of the second optical path 205 longer than the optical path length of the first optical path 203, the second FPN is generated at a position separated from the zero delay from the first FPN.

The FPN generation optical system 200 may include an optical path splitting member 202 (for example, an optical splitter), and the optical path splitting member 202 may be provided for splitting the optical path on the light source side into the first optical path 203 and the second optical path 205. The first optical member 204 may be disposed in the first optical path 203 split by the optical path splitting member 202, and the second optical member 206 may be disposed in the second optical path split by the optical path splitting member 202.

The first optical path 203 and the second optical path 205 have optical path lengths different from each other. In other words, the optical path length from the branching position of the optical path splitting member 202 to the first optical member 204 is different from the optical path length from the branching position of the optical path splitting member 202 to the second optical member 206. As a result, the first FPN formed by the first optical member 204 and the second FPN formed by the second optical member 206 are formed at different positions in the depth direction on an OCT image. In addition, the distance between the first FPN and the second FPN in the depth direction is caused by the optical path length difference between the first optical path 203 and the second optical path 205.

In addition, the first optical path 203 and the second optical path 205 are set (constructed) to have optical dispersion amounts equal to each other. As a result, based on mapping information (hereinafter, first wavenumber mapping information) of each of the wavenumber components calculated using the first FPN and mapping information (hereinafter, second wavenumber mapping information) of each of the wavenumber components calculated using the second FPN, when obtaining the correction information for correcting the mapping state of each of the wavenumber components by an arithmetic operation, the dispersion component included in each piece of mapping information can be appropriately canceled, and thus, it is possible to obtain the correction information with high accuracy (will be described in detail later). In this case, it is not necessarily required that the dispersion amounts which are equal to each other are strictly the same as each other, and it is only necessary to ensure a certain accuracy and appropriately cancel the dispersion component.

Polarization Adjustment Mechanism

In the OCT optical system 100 of the present example, a plurality of polarization adjustment sections may be provided, and for example, in the optical path of the OCT optical system 100, a first polarization adjustment section 300, a second polarization adjustment section 302, and a third polarization adjustment section 304 may be provided (refer to FIG. 1).

The first polarization adjustment section 300 may be disposed in the optical path of the first reference optical path 110a and may be provided for adjusting the polarization state of the reference light through the first reference optical path 110a. The second polarization adjustment section 302 may be disposed in the optical path of the second reference optical path 110b and may be provided for adjusting the polarization state of the reference light through the second reference optical path 110b. The third polarization adjustment section 304 may be disposed in the FPN generation optical system 200 and may be provided for adjusting the polarization state of the light passing through the optical path of the FPN generation optical system 200.

Acquisition of Depth Information

When the emitted wavelength is changed by the light source 102, the interference signal light that corresponds thereto is received by the detector 120, and as a result, the light is detected by the detector 120 as a spectrum signal. The control section 70 processes (Fourier analysis) the spectrum signal detected by the detector 120 and obtains the OCT data of the examinee's eye.

The spectrum signal (spectral data) may be rewritten as a function of a wavelength $\lambda$ and may be transformed into a function $I(k)$ that is equally spaced with respect to a wavenumber $k(=2\pi/\lambda)$. Alternatively, the equally spaced function $I(k)$ with respect to the wavenumber k from the beginning may be acquired (K-CLOCK technology). The control section 70 may obtain the OCT data in the depth (Z) region by Fourier transforming the spectrum signal in the wavenumber k space.

Furthermore, the information after the Fourier transform may be expressed as a signal including a real number component and an imaginary number component in a Z space. The control section 70 may obtain the OCT data by obtaining absolute values of the real component and the imaginary component in the signal in the Z space.

In the present example, the control section 70 may process the first interference signal detected by the first detector 120a and obtain the first OCT data, and may process the second interference signal detected by the second detector 120b and obtain the second OCT data. Here, in a case where the first reference optical path 110a and the second reference optical path 120b are set to have optical path lengths different from each other, regarding the first OCT data and the second OCT data, the OCT data in a region of which at least a part thereof is different in the depth direction is acquired. In a case where the first reference optical path 110a and the second reference optical path 120b are set to have the same optical path lengths, regarding the first OCT data and the second OCT data, the OCT data in a region which is the same in the depth direction is acquired.

Control System

The control section 70 may include a CPU (processor), a RAM, a ROM, and the like (refer to FIG. 1). For example, the CPU of the control section 70 may control the OCT apparatus. The RAM temporarily stores various types of information. Various programs for controlling the operation of the OCT apparatus, initial values, and the like may be stored in the ROM of the control section 70.

The nonvolatile memory (hereinafter shortened to "memory") 72 that serves as a storage section, the display section 75, and the like may be electrically connected to the control section 70. As the memory 72, a non-fugitive storage medium which is capable of holding stored contents even when the supply of power is stopped may be used. For example, as the memory 72, a USB memory or the like which is attachably and detachably mounted to a hard disc drive, a flash ROM, and the OCT apparatus, can be used. In the memory 72, a control program for controlling the acquisition of the OCT data and the capturing of the OCT image may be stored, an arithmetic processing program for combining the OCT image using the FPN and an arithmetic processing program which obtains the correction information for correcting the mapping state of each of the wavenumber components, and the like, may be stored. In addition to the OCT image generated from the OCT data, various types of information related to the capturing may be stored in the memory 72. The display section 75 may display the OCT image generated from the OCT data.

Image Composition Using FPN

Figure 3:
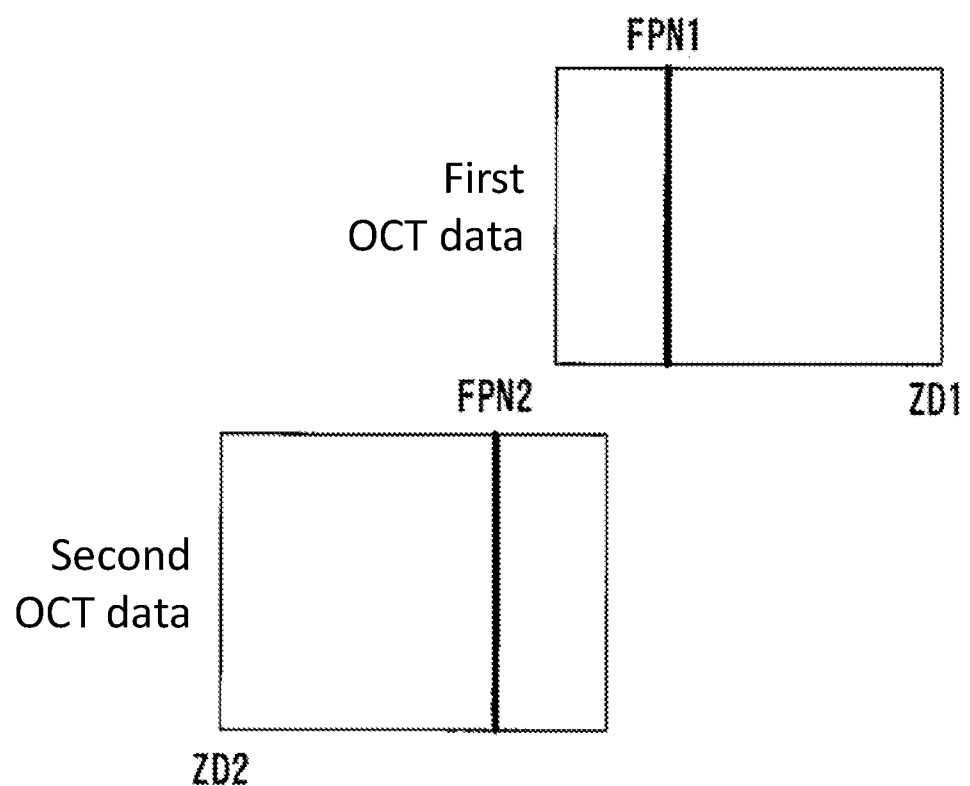
FIG. 3 is a diagram showing an example of data obtained in a case of synthesizing a plurality of OCT data by using an FPN signal and a diagram showing the data before synthesizing.
Figure 4:
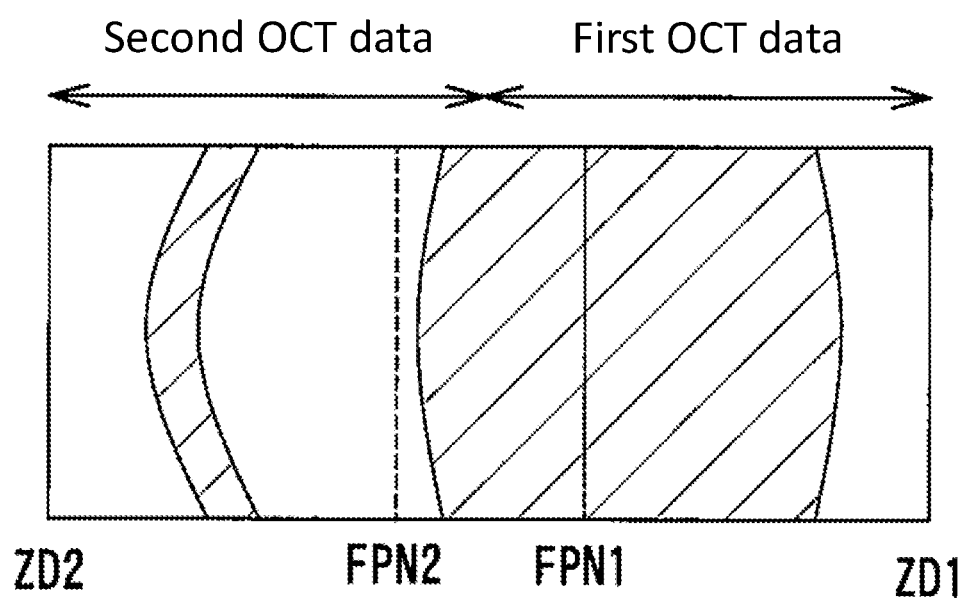
FIG. 4 is a diagram showing an example of data obtained in a case of synthesizing the plurality of OCT data by using the FPN signal and a diagram showing the data after synthesizing.
Figure 5:
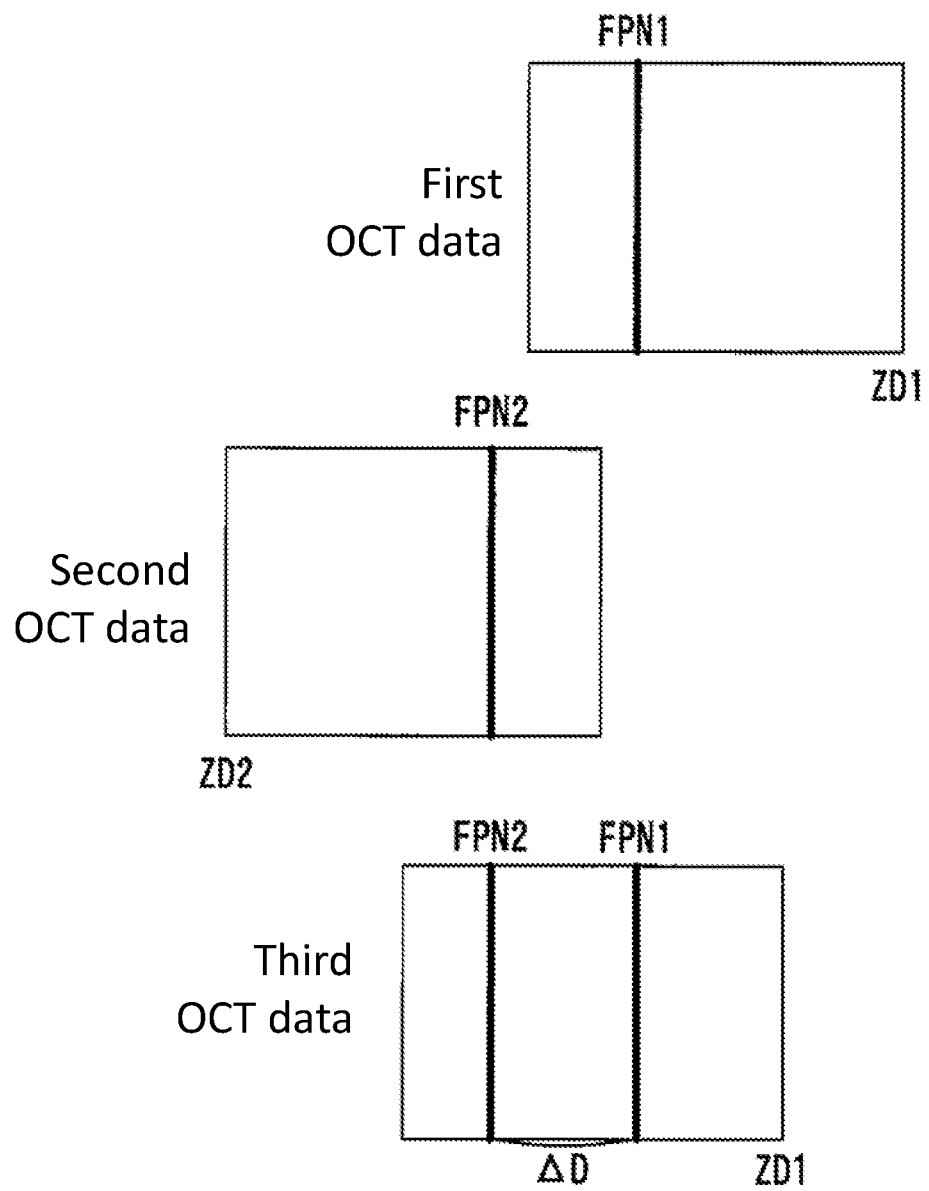
FIG. 5 is a diagram showing an alteration example of data obtained in a case of synthesizing the plurality of OCT data by using the FPN signal.

In this case, the control section 70 may obtain the combined OCT data, for example, by combining the first OCT data based on the first interference signal and the second OCT data based on the second interference signal, based on the FPN signal detected by the first detector 120a and the FPN signal detected by the second detector 120b (refer to FIGS. 3 to 5). In other words, the FPN signal may be used as a reference signal for combining the plurality of OCT data. Here, in the second OCT data, at least a part of the depth region on the examinee's eye may be different from that in the first OCT data.

As an example, since the disposition position of the optical members (for example, the optical members 204 and 206) for FPN generation is already known in the FPN generation optical system 200, the positional relationship between the first OCT data and the second OCT data may be set using the FPN signal.

According to this, it is possible to appropriately set the positional relationship between the first OCT data and the second OCT data. In addition, in the present example, since the first OCT data is detected by the first detector 120a and the second OCT data is detected by the second detector 120b at the same time, it is possible to reduce the position shift caused by the movement or the like of the examinee's eye.

For example, the FPN generation optical system 200 may be an FPN generation optical system which includes at least the first optical member (for example, first optical member 204) which generates the first FPN and the second optical member (for example, second optical member 206) which generates the second FPN at a position different from that of the first FPN, and generates at least two FPN signals.

The control section 70 may obtain the combined OCT data by combining the first OCT data based on the first interference signal and the second OCT data based on the second interference signal, based on the FPN by the first optical member which is detected by the first detector 120a and the FPN by the second optical member detected by the second detector 120b.

FIGS. 3 and 4 are views illustrating an example of data in a case of combining the plurality of OCT data using the FPN signal, and FIG. 3 is an image view of a state before the combining and FIG. 4 is an image view of a state after the combining. FPN 1 is the FPN signal generated by the first optical member 204 and FPN 2 is the FPN signal generated by the second optical member 206.

In FIG. 3, the FPN 1 is formed in the first OCT data and the FPN 2 is formed in the second OCT data. The first OCT data may be acquired using the first reference optical path 110a and the first detector 110a and the second OCT data may be acquired using the second reference optical path 110b and the second detector 110b.

In a case of setting the positional relationship between the OCT data using the FPN signal, the control section 70 sets the positional relationship between the OCT data, for example, using the FPN 1 included in the first OCT data and the FPN 2 included in the second OCT data. Here, the control section 70 may detect the position of FPN in the depth direction and may combine the plurality of OCT data with reference to the detection position of the FPN (refer to FIG. 4).

Here, since the positional relationship between the first optical member 204 and the second optical member 204 is already known (for example, the optical path length ΔD), in a case of combining the first OCT data and the second OCT, the control section 70 may detect the positions of the FPN 1 and the FPN 2 and may combine the data such that the detected position of the FPN 1 and the detected position of the FPN 2 are separated from each other by the optical path length ΔD separation. In addition, regarding the composition at the overlapping part between the plurality of OCT data, any one piece of OCT data may be used, or an average of both OCT data may be obtained.

The control section 70 may measure the dimensions (for example, anterior chamber depth and eye axial length) of the examinee's eye based on the combined OCT data combined as described above, and may further display the obtained measurement result on the display section 75.

FIG. 5 is a view illustrating a modification example of data in a case of combining the plurality of OCT data using the FPN signal, and the FPN 1 and the FPN 2 are formed in third OCT data. Here, the third OCT data may be acquired using the first reference optical path 110a and the first detector 110a, and by adjusting the optical path length of the first reference optical path 110a, the third OCT data may be acquired.

Here, the control section 70 may set the positional relationship between the first OCT data and the second OCT data using the third OCT data. In this case, the control section 70, for example, may set the positional relationship such that the detection position of the FPN 1 on the first OCT data and the detection position of the FPN 1 on the third OCT data are at the same position in the depth direction, and further, the control section 70, for example, may set the positional relationship such that the detection position of the FPN 2 on the second OCT data and the detection position of the FPN 2 on the third OCT data are the same position in the depth direction. According to this, even when the position of the optical member for FPN generation fluctuates due to secular change, since the actual positional relationship can be used, the positional relationship between the first OCT data and the second OCT data can be more stably set.

In addition, in a case of detecting the position of the FPN in the depth direction, for example, the control section 70 may process the OCT data acquired by the detectors 120a and 120b, and may extract the FPN signal by the optical member (for example, the first optical member 204 or the second optical member 206) for FPN generation. Since the signal intensity of the FPN signal is already known, the control section 70 determines, for example, whether or not each luminance signal of the OCT data exceeds a threshold value set for obtaining the FPN signal, and can extract the FPN signal (reference signal) that corresponds to the optical member for FPN generation. In addition, the FPN 1 and the FPN 2 can be determined using a known disposition.

Figure 6:
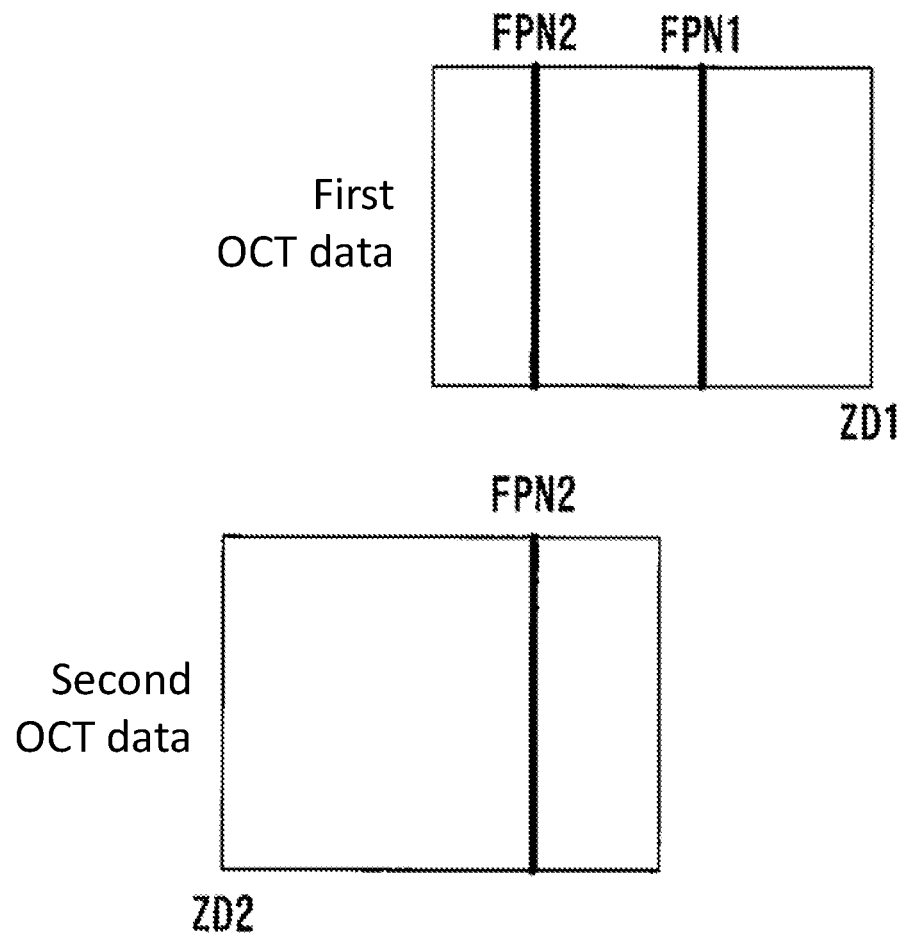
FIG. 6 is a diagram showing an alteration example of data obtained in a case of synthesizing the plurality of OCT data by using the FPN signal.

In addition, not being limited to the above-described method, the third OCT data in FIG. 5 which is used as the first OCT data, and the second OCT data in FIG. 5 may be combined (refer to FIG. 6). In this case, the FPN 1 and the FPN 2 are formed in the first OCT data and the FPN 2 is formed in the second OCT data. The first OCT data may be acquired using the first reference optical path 110a and the first detector 110a and the second OCT data may be acquired using the second reference optical path 110b and the second detector 110b.

In this case, the control section 70 may detect the position of the FPN 2, may set the positional relationship between the OCT data using the detected position, and may set the positional relationship by matching the FPN 2 of the first OCT data and the FPN 2 of the second OCT data by image processing. In this case, the control section 70 may perform the composition such that the FPN 1 of the first OCT data and the FPN 1 of the second OCT data are identical to each other in the depth direction in the combined OCT data.

In addition, in the present example, regarding the FPN generation optical system 200, the first optical path 203 on which the first optical member 204 is disposed and the second optical path 205 on which the second optical member 206 is disposed are set (constructed) to have the optical dispersion amounts equal to each other. As a result, since the decrease of the signal intensity (SNR) of the FPN can be reduced, it is possible to perform the composition of the OCT data using the FPN.

FIG. 6 can also be considered as an example of image composition using one FPN. Generation of the FPN 1 is not necessarily indispensable. In other words, even in a case where an FPN optical system 200 of the present example includes one optical member for FPN generation, image composition is possible and the configuration of the apparatus can be simplified, but as compared with a case of using the plurality of FPN signals, the capturing range in the depth direction becomes narrow and the number of overlapping regions between different OCT data increases. Meanwhile, in a case of providing a common region, by using the plurality of FPN signals, it is possible to widen the imaging range in the depth direction and to reduce the overlapping region between different OCT data.

In addition, with respect to the FPN generation optical system 200 according to the present example, since the optical members (for example, the first optical member 204 and the second optical member 206) for FPN generation used for combining the OCT data are arranged in the air, the FPN generated by the surface reflection is used for image composition, and as a result, since it is possible to reduce the signal intensity (SNR) of FPN or the like, it is possible to accurately combine the OCT data using the FPN.

In addition, the timing of obtaining the FPN signal may be, for example, the time when turning on the power or may be every time the examinee is changed. Further, the timing of obtaining the FPN signal may be the time of optimization control for optimizing the capturing conditions in the OCT optical system. Naturally, not being limited thereto, the timing of obtaining the FPN signal may be any time. For example, in the control section, the OCT data including the FPN signal is acquired in advance, and the composition of the OCT data acquired later, correction of the mapping state, polarization adjustment and the like may be performed using the FPN signal acquired in advance.

Light Shielding Member

In addition, by disposing a light shielding member or a light reducing member in the optical path of the FPN generation optical system 200, the FPN signal of the OCT data used for observing or capturing the examinee's eye may be reduced. In this case, the FPN signal on the OCT data may be reduced as at least one of the first optical path and the second optical path is shielded or dimmed. These are effective in a case of obtaining the OCT data used for diagnosis, observation or the like. In addition, not being limited thereto, the FPN signal included in the OCT data may be removed by signal processing.

Wavenumber Mapping Correction

Figure 7:
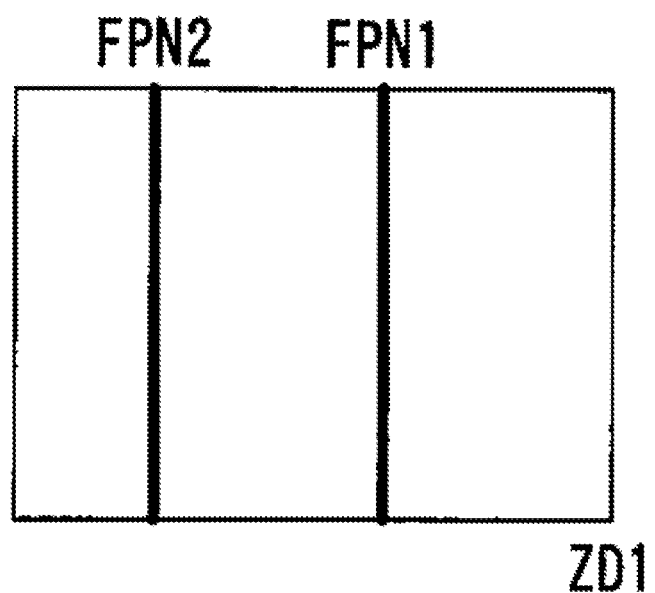
FIG. 7 is a diagram showing an example of the OCT data that is used in wavenumber mapping correction.

FIG. 7 is a view illustrating an example of the OCT data according to the present example in which the first FPN signal and the second FPN signal are simultaneously formed on the OCT data. In addition, the OCT image of the examinee's eye may be included on the OCT data.

In this case, the control section 70 may process the signal including both the first FPN and the second FPN at the same time, and may acquire correction information for correcting the mapping state of each of the wavenumber components. In other words, the control section 70 may be used, for example, as an arithmetic processor for obtaining the correction information. In addition, the correction information may also be acquired by a processor different from the control section that drives the OCT optical system. Further, the control section 70 may generate the correction information using a phase difference information of at least two FPN signals accompanying sweeping of the wavelength by the light source 102, for example, during capturing or before capturing the OCT image.

More specifically, the control section 70 may correct the mapping state (wavenumber sampling mapping) of each wavelength component (wavenumber components) with respect to a sampling point p based on at least two FPN signals generated by the FPN generation optical system 200.

For example, by analyzing the intensity level of the FPN, the control section 70 may obtain $\phi(k)$ in the spectrum signal at the position that corresponds to the FPN. $\phi(k)$ indicates a change in phase $\phi$ of the spectrum signal in accordance with the sweep wavelength (wavenumber). $\phi(k)$ may be expressed by a function that has the horizontal axis indicating the wavenumber k and the vertical axis indicating the phase $\phi$. Polynomial fitting may be performed on $\phi(k)$ in the wavenumber k region with large signal intensity (amplitude), and $\phi(k)$ in the wavenumber k region with small signal intensity may be obtained by extrapolation or interpolation. For example, $\phi(k)$ may be obtained from ArcTangent (arctangent) of the ratio of the real part RealF to the imaginary part ImagF of the Fourier transform value (intensity value) F at the depth position that corresponds to FPN. Here, the arctangent of the ratio between the real part and the imaginary part of the Fourier transform value is calculated by ArcTangent processing, and $\phi(k)$ is obtained.

Figure 8:
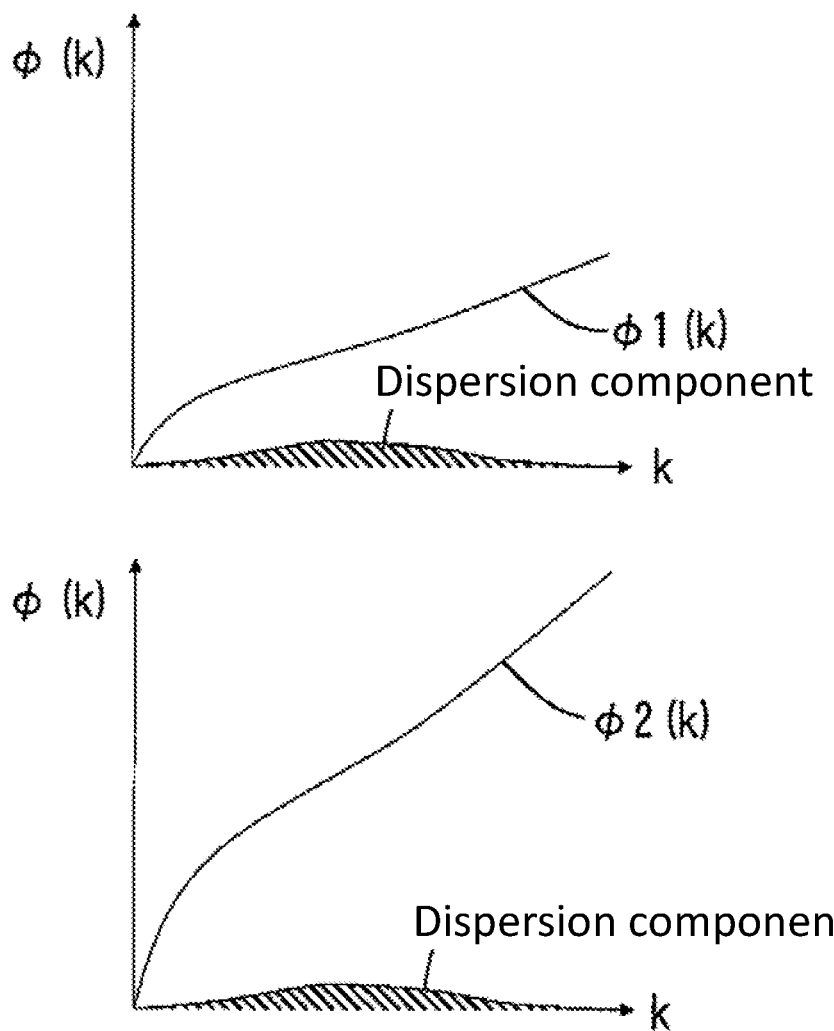
FIG. 8 shows graphs of an example of wavenumber mapping information obtained by processing FPN.

In a case where at least two FPN signals are simultaneously obtained, the control section 70 may process the first FPN and obtain first wavenumber mapping information $\phi 1(k)$, and may process the second FPN and obtain second wavenumber mapping Information $\phi 2(k)$ (refer to FIG. 8). In this case, each wavenumber mapping information may be obtained as phase information of each of the wavenumber components.

Furthermore, the control section 70 may obtain the difference information $\Delta \phi(k)$ between the first wavenumber mapping information $\phi 1(k)$ and the second wavenumber mapping information $\phi 2(k)$ (refer to FIG. 5). In addition, the wavenumber mapping information may be obtained as the phase difference information of each of the wavenumber components. In a case of obtaining the difference information $\Delta \phi(k)$, the difference information may be obtained with $\Delta \phi(k)=\phi 2(k)-\phi 1(k)$ since the phase advance of the second FPN is earlier. In addition, by obtaining the difference information, the dispersion component included in each wavenumber mapping information can be canceled. In this case, as described above, it is preferable that the dispersion amount between the first optical path 203 and the second optical path 205 be equal to each other.

Here, assuming that the optical distance (optical path length difference) between the first FPN and the second FPN is $\Delta Z$, and when the difference information $\Delta \phi(k)$ is ideal, a straight line as illustrated in the following equation (7) is achieved.

$$\Delta \phi(k) = \Delta Z k \quad (7)$$

Here, $\Delta Z$ is obtained as follows. An interference component can be generalized as $\exp(ikz)$, and k and z have a relationship of $kz=2\pi$. From this point of view, z can be expressed as the following equation (8), where N is the number of sampling points and kmax and kmin are the maximum value and the minimum value of the k value detected at each sampling point.

$$z = \frac{2\pi \cdot i}{k_{max} - k_{min}} \quad (8)$$

In addition, i=0, 1, 2, . . . , N/2 is achieved.

Here, assuming that the interference signal that corresponds to $\Delta Z$ is detected at the sampling point that corresponds to $i(\Delta Z)$, $\Delta Z$ can be expressed by the following expression (9).

$$\Delta Z = \frac{2\pi \cdot i(\Delta Z)}{k_{max} - k_{min}} \quad (9)$$

Since $\Delta \phi(k)$ is supposed to ideally be a straight line with slope $\Delta Z$ and intercept 0, when second and third order nonlinear terms are $\sigma$, k is corrected to the following equation (10).

$$k' = k + \frac{\sigma}{\Delta z} \quad (10)$$

After this, the corrected wavelength $\lambda'$ is determined as $\lambda'=2\pi/k'$. Here, $\sigma$ is the nonlinear term $\sigma=b_2k^2+b_3k^3$ when expanded to the following equation (11).

$$\phi(k) = \sum_{i=0}^{3} b_i k^i \qquad (11)$$

In addition, in the above-described example, the nonlinear term is third order, but not being limited thereto, and more nonlinear terms may be adopted. For example, approximately ninth order may also be adopted. Otherwise, other fitting methods (chirped sine wave fitting method) may be used.

Figure 9:
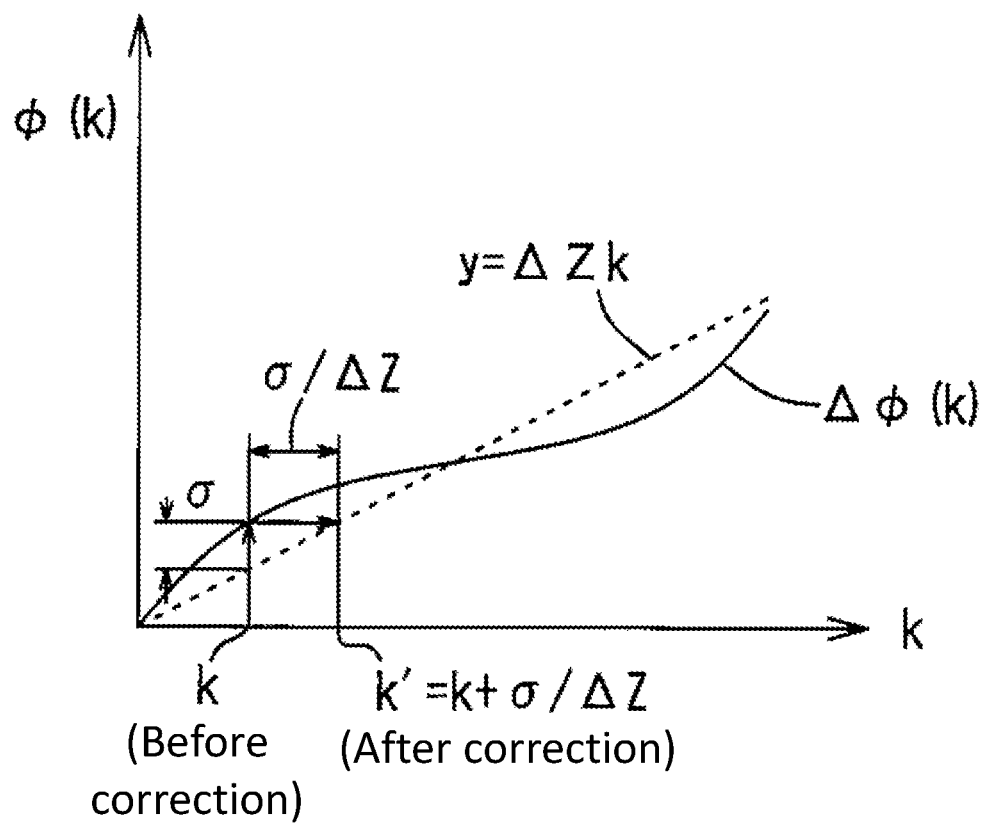
FIG. 9 is a graph showing an example for correcting a mapping state in a case of obtaining difference information $\Delta\phi$ (k) between first wavenumber mapping information $\phi 1$ (k) and second wavenumber mapping information $\phi 2$ (k).

In addition, FIG. 9 is a view schematically illustrating the mapping of the spectrum signal to be corrected by performing the correction calculation. In addition, when the corrected values of $\Delta\phi(kmin)$ and $\Delta\phi(kmax)$ are within a predetermined allowable range (for example, approximately $1E^{-5}$) from the ideal values $z(peak)\cdot kmin$, $z(peak)\cdot kmax$, convergence is determined, and when the condition is not satisfied, the same calculation is repeated using the corrected $\lambda'$ described above.

As described above, the control section 70 may obtain the correction information from at least two FPN signals generated using the FPN generation optical system 200 by the arithmetic operation, and may store the obtained correction information in the memory 72. Accordingly, the correspondence relationship between each wavelength component detected by the detector 120 and each sampling point can be more accurately obtained. The obtained correction information may be used for acquiring OCT data. In addition, the method of obtaining $\phi(k)$ from the FPN and the method of obtaining the wavenumber mapping information, reference should be made to JP-A-2013-156229, JP-A-2015-68775, and the like.

In addition, in the description above, a case where the wavenumber mapping information is corrected in the SS-OCT is described, but the invention is not limited thereto, and the present example can also be applied in a case where the wavenumber mapping information is corrected in the SD-OCT. In this case, for example, the control section 70 may correct the mapping state of each wavelength (wavenumber) with respect to each sampling point of spectrometer based on at least two FPN signals generated by the FPN generation optical system 200. In this case, reference may be made to JP-A-2010-220774.

In addition, refer to JP-A-2017-017156 for the wavenumber mapping correction according to the present example.

In addition, the timing of obtaining the correction information for correcting the mapping state of each of the wavenumber components, for example, may be the time when turning on the power or may be every time the examinee is changed. Further, the timing of acquiring the FPN signal may be the time of optimization control for optimizing the capturing conditions in the OCT optical system. Naturally, not being limited thereto, the timing of obtaining the FPN signal may be any time. In addition, after correcting the mapping state, the FPN on the OCT image may be removed by noise removal processing.

In addition, in the description above, the FPN generation optical system is provided at a position branched from the measurement optical path. However, the invention is not limited thereto as long as the FPN generation optical system is in the optical path of the OCT optical system. For example, the FPN generation optical system may be disposed at a position branched from the reference optical path of the OCT optical system. In this case, for example, the FPN signal due to interference between the light from the FPN generation optical system and the reference light (or the measurement light) may be obtained. Further, for example, the FPN generation optical system may be disposed at a position branched from the optical path after the measurement optical path and the reference optical path join together. In this case, for example, the FPN signal due to the interference between the interference light directly toward the optical path of the interference light and the interference light from the FPN generation optical system provided at a position branched from the optical path of the interference light may be obtained, and may be detected by the detector 120. In addition, in a case where the detector 120 includes the first detector 120a and the second detector 120b, the FPN generation optical system is disposed before being split into the optical paths of each of the detectors, and accordingly, similar FPN signals may be detected by each of the detectors.

Application Example to Examinee's Eye

The apparatus may be an ophthalmic OCT apparatus that obtains OCT data of the examinee's eye. For example, as the ophthalmic OCT apparatus, a configuration may be employed, in which it is possible to acquire the OCT data of the fundus and the OCT data of the anterior chamber including the cornea and the crystalline lens, or a configuration may be employed, in which it is possible to measure an eye axial length based on the OCT data of the cornea and the fundus.

For example, the ophthalmic OCT apparatus may be configured to be capable of automatically or manually switching optical disposition of an OCT optical system 100 in response to a mode switching signal. Hereinafter, an example of a case of performing mode switching between a fundus imaging mode, an anterior chamber imaging mode, and an eye axial length measuring mode will be described.

Fundus Imaging Mode

In a case where the fundus imaging mode is set, a control unit 70 may control a light guiding optical system 150 and switch the disposition to the optical disposition for obtaining the OCT data of the fundus. In this case, the control unit 70 may switch the optical disposition of the light guiding optical system 150 such that the turning point of the measurement light is formed on the pupil of the examinee's eye and the concentrating position of the measurement light is formed on the fundus, for example. For example, a configuration according to the switching of the optical disposition of the light guiding optical system 150 is described in JP-A-2016-209577, other than a chapter <configuration related to switching of optical disposition of light guiding optical system> to be described below.

In a case where the fundus imaging mode is set, a control unit 70 may adjust an optical path length of at least one of the measurement light and the reference light and set an acquisition region of the OCT data in the fundus. In this case, the control unit 70 may adjust an optical path length difference between the measurement light and the reference light such that an optical path length of the reference light having passed through at least any one of a plurality of reference optical paths matches an optical path length of the measurement light having passed through the fundus, for example. In a case where the optical path length difference is adjusted, the optical path length difference may be adjusted to acquire the OCT data in a state in which a retina is formed deeper than the zero-delay position or may be adjusted to acquire the OCT data in a state in which a choroid is formed closer to a front side than the zero-delay position.

For example, in the example, an optical member disposed on the measurement optical path may be moved such that the optical path length of the measurement light from the fundus matches that of the reference light from a first reference optical path 110a, and thereby the optical path length of the measurement light may be adjusted. Consequently, the OCT data of the fundus is included in first OCT data that is obtained based on an output signal from at least a first detector 110a.

Figure 10:
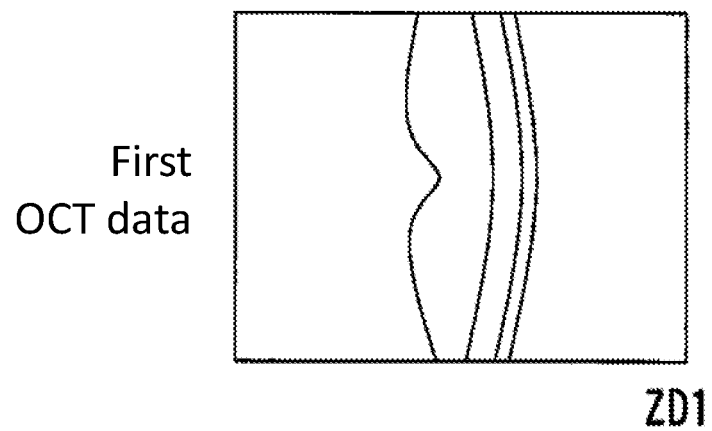
FIG. 10 is a diagram showing an example of OCT data that is acquired in a fundus imaging mode.
Figure 10:
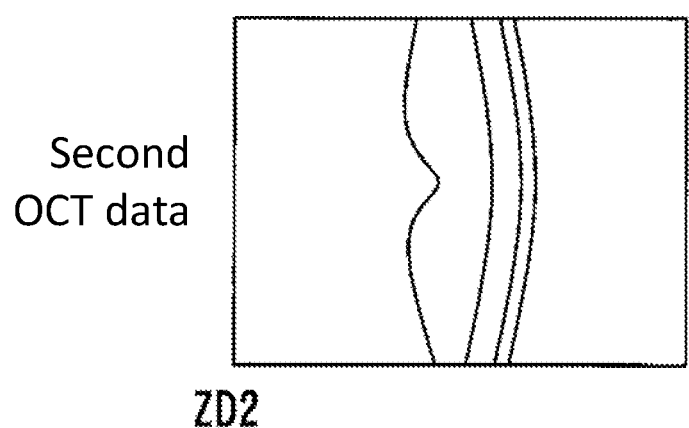

FIG. 10 is a diagram showing an example of the OCT data that is acquired in the fundus imaging mode. The control unit 70 may move an optical member 112 and adjust an optical path length of a second reference optical path 110b such that the optical path length thereof is equal to the optical path length of the first reference optical path 110a. As a result, the first OCT data based on the first detector 110a and second OCT data based on a second detector 110b indicate the same region in the fundus. In this case, the control unit 70 may acquire synthetic OCT data (for example, averaged image, a super resolution image, and the like) based on the first OCT data and the second OCT data. Consequently, the OCT data of the fundus related to a predetermined imaging region is smoothly obtained in a short time.

Eye Axial Length Measuring Mode

In a case where the eye axial length measuring mode is set, the control unit 70 may control the light guiding optical system 150 and switch the disposition to the same optical disposition as that of the fundus imaging mode described above. In this case, the control unit 70 may switch the optical disposition of the light guiding optical system 150 such that the turning point of the measurement light is formed on the pupil and the concentrating position of the measurement light is formed on the fundus, for example. Consequently, in the OCT data that is obtained during measurement of an eye axial length, it is possible to acquire shape information (for example, information in the vicinity of a macula) of the fundus in detail and, as a result, it is possible to measure the eye axial length of the examinee's eye with high accuracy.

In a case where the eye axial length measuring mode is set, the control unit 70 may adjust an optical path length of at least one of the measurement light and the reference light, set an acquisition region of the OCT data in the fundus by one of the first detector 120a and the second detector 120b, and set an acquisition region of the OCT data in the cornea by the other of the first detector 120a and the second detector 120b.

Figure 11:
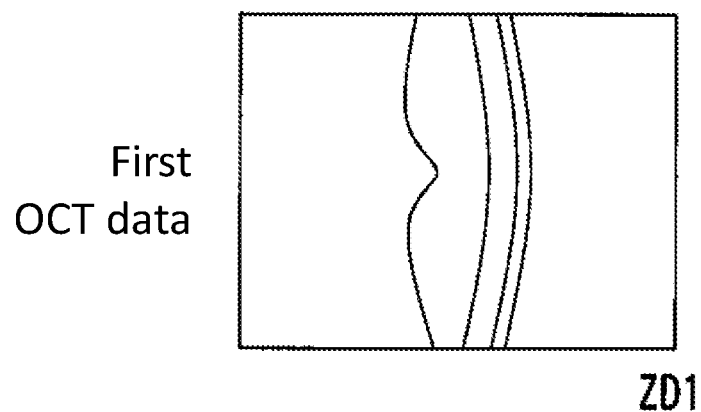
FIG. 11 is a diagram showing an example of OCT data that is acquired in an eye axial length imaging mode.
Figure 11:
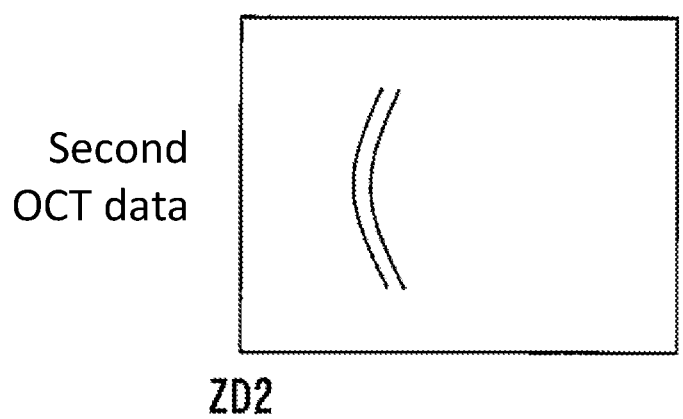

FIG. 11 is a diagram showing an example of the OCT data that is acquired in an eye axial length imaging mode. For example, in the example, an optical member disposed on the measurement optical path may be moved such that the optical path length of the measurement light from the fundus matches that of the reference light from the first reference optical path 110a, and thereby the optical path length of the measurement light may be adjusted. Consequently, the OCT data of the fundus is included in the first OCT data that is obtained based on the output signal from at least the first detector 110a.

In a state in which the position of the optical member disposed on the measurement optical path is adjusted such that the OCT data of the fundus is included in the first OCT data, the control unit 70 may move the optical member 112 disposed on the second reference optical path 110b such that the optical path length of the measurement light from the cornea matches that of the reference light from the second reference optical path 110b, and thereby the control unit may adjust the optical path length of the reference light of the second reference optical path 110b. Consequently, the OCT data of the cornea is included in the second OCT data that is obtained based on the output signal from the second detector 110b.

When the OCT data of the fundus and the OCT data of the cornea are acquired, the control unit 70 may detect a retina position based on the OCT data of the fundus and detect a cornea position based on the OCT data of the cornea. The control unit 70 may measure the eye axial length by using a detection result of the retina position, a detection result of the cornea position, and an optical path length difference between the first reference optical path 110a and the second reference optical path 110b.

In this case, the optical path length difference between the first reference optical path 110a and the second reference optical path 110b may be obtained by a drive position of a drive unit for moving the optical member 112 or may be detected based on the position of the optical member 112. In a case where the optical path length difference between the first reference optical path 110a and the second reference optical path 110b is constant, a known optical path length difference may be used. In addition, the method of obtaining the difference is not limited thereto, and an FPN generating optical system 200 may be configured to include an FPN generating optical member that generates an FPN signal corresponding to the cornea and an FPN generating optical member that generates an FPN signal corresponding to the fundus, and the optical path length difference may be acquired by using the known position of the optical member. In this case, three or more FPN generating optical members may be used to correspond to optical path length differences.

Anterior Chamber Imaging Mode

In a case where the anterior chamber imaging mode is set, the control unit 70 may control the light guiding optical system 150 and switch the disposition to the optical disposition for obtaining the OCT data of the anterior chamber including the cornea and the crystalline lens. In this case, the control unit may switch the optical disposition of the light guiding optical system 150 such that the turning point of the measurement light is formed closer to the side of the apparatus than the pupil of the examinee's eye and the concentrating position of the measurement light is formed on the anterior chamber. For example, a configuration according to the switching of the optical disposition of the light guiding optical system 150 is described in JP-A-2016-209577.

In a case where the anterior chamber imaging mode is set, the control unit 70 may adjust the optical path length of at least one of the measurement light and the reference light, set an acquisition region of the OCT data in the crystalline lens by one of the first detector 120a and the second detector 120b, and set an acquisition region of the OCT data in the cornea by the other of the first detector 120a and the second detector 120b. Here, the OCT data that is acquired by the first detector 120a and the OCT data that is acquired by the second detector 120b are different from each other in at least a part of the acquisition region on the examinee's eye in the depth direction. Consequently, OCT data including a cornea region and OCT data including a crystalline lens region may be acquired. In this case, at least the cornea and a crystalline lens front surface may be included in the OCT data including the cornea region, and at least a crystalline lens rear surface may be included in the OCT data including the crystalline lens region. That is, the OCT data of a front side region in the anterior chamber region and the OCT data of a rear side region in the anterior chamber region may be individually acquired.

For example, the control unit 70 may synthesize the OCT data the crystalline lens region and the OCT data including the cornea region. In this case, a synthesis process using the FPN signal described above may be used, or the optical path length of the FPN generating optical system 200 may be set such that the optical path length of the measurement light from the cornea and the crystalline lens matches the optical path length of the measurement light having passed through the FPN generating optical system 200. In other words, in a state in which the optical path length difference between the measurement light and the reference light of the light guiding optical system 150 is set such that it is possible to acquire the OCT data including the cornea region and the OCT data including the crystalline lens region, the FPN generating optical system 200 may be set such that an FPN signal is included in each of the OCT data.

In a case where the optical path length difference is adjusted, the optical path length difference may be adjusted to acquire the OCT data including the cornea region in a state in which a cornea front surface is formed deeper than the zero-delay position or may be adjusted to acquire the OCT data including the crystalline lens region in a state in which a crystalline lens rear surface is formed closer to the front side than the zero-delay position. Consequently, it is possible to avoid an influence due to a mirror image during image synthesis. In addition, the optical path length difference between the first reference optical path 110*a* and the second reference optical path 110*b* may be set such that parts of the acquisition region on the examinee's eye in the depth direction overlap each other between the first OCT data and the second OCT data. Consequently, it is possible to smoothly perform connection in the image synthesis.

Figure 12:
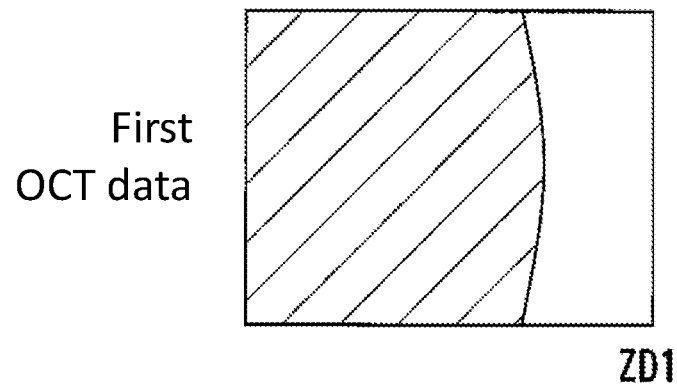
FIG. 12 is a diagram showing an example of OCT data that is acquired in an anterior chamber imaging mode.
Figure 12:
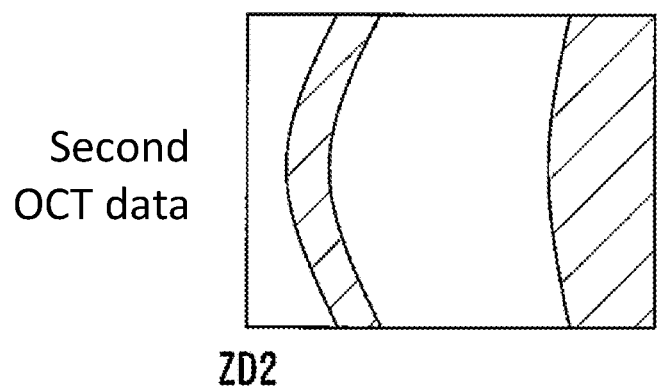

FIG. 12 is a diagram showing an example of the OCT data that is acquired in the anterior chamber imaging mode. For example, in the example, an optical member disposed on the measurement optical path may be moved such that the optical path length of the measurement light from the crystalline lens matches that of the reference light from the first reference optical path 110*a*, and thereby the optical path length of the measurement light may be adjusted. Consequently, the OCT data of the crystalline lens region is included in the first OCT data that is obtained based on the output signal from at least the first detector 110*a*.

In a state in which the position of the optical member disposed on the measurement optical path is adjusted such that the OCT data of the crystalline lens is included in the first OCT data, the control unit 70 may move the optical member 112 disposed on the second reference optical path 110*b* such that the measurement length of the measurement light from the cornea matches that of the reference light from the second reference optical path 110*b*, and thereby the control unit may adjust the optical path length of the reference light of the second reference optical path 110*b*. Consequently, the OCT data of the cornea is included in the second OCT data that is obtained based on the output signal from the second detector 110*b*.

When the OCT data of the crystalline lens and the OCT data of the cornea are acquired, for example, the control unit 70 may synthesize the OCT data of the crystalline lens with the OCT data of the cornea and acquire synthesized OCT data. Further, the control unit 70 may detect the cornea position, the crystalline lens position, and the like based on the synthesized OCT data and measure an anterior chamber depth, a crystalline lens thickness, or the like of the examinee's eye.

Correction of OCT Data by Using FPN Signal Included in Other OCT Data

The control unit 70 may acquire OCT data including the FPN signal in one of the first OCT data and the second OCT data and acquire OCT data that does not include the FPN signal in the other of the first OCT data and the second OCT data. In addition, the control unit 70 may obtain wavenumber mapping information based on the FPN signal in the OCT data including the FPN signal so as to correct the OCT data that does not include the FPN signal. According to the corresponding configuration, in a case of using the plurality of detectors, it is not always necessary to provide the FPN generating optical system corresponding to the detectors. In this case, the control unit 70 may correct the OCT data that does not include the FPN signal in real time, and thereby it is possible to correct the OCT data with higher accuracy.

In this case, the control unit 70 may adjust the optical path length of at least one of the measurement light and the reference light and set an acquisition region of the OCT data in a predetermined imaging site (for example, the fundus, the cornea, or the crystalline lens) by one of the first detector 120*a* and the second detector 120*b*. In addition, the control unit 70 sets an acquisition region of the OCT data on an optical member (for example, an optical member 204 or an optical member 206) of the FPN generating optical system 200 by the other of the first detector 120*a* and the second detector 120*b*.

Figure 13:
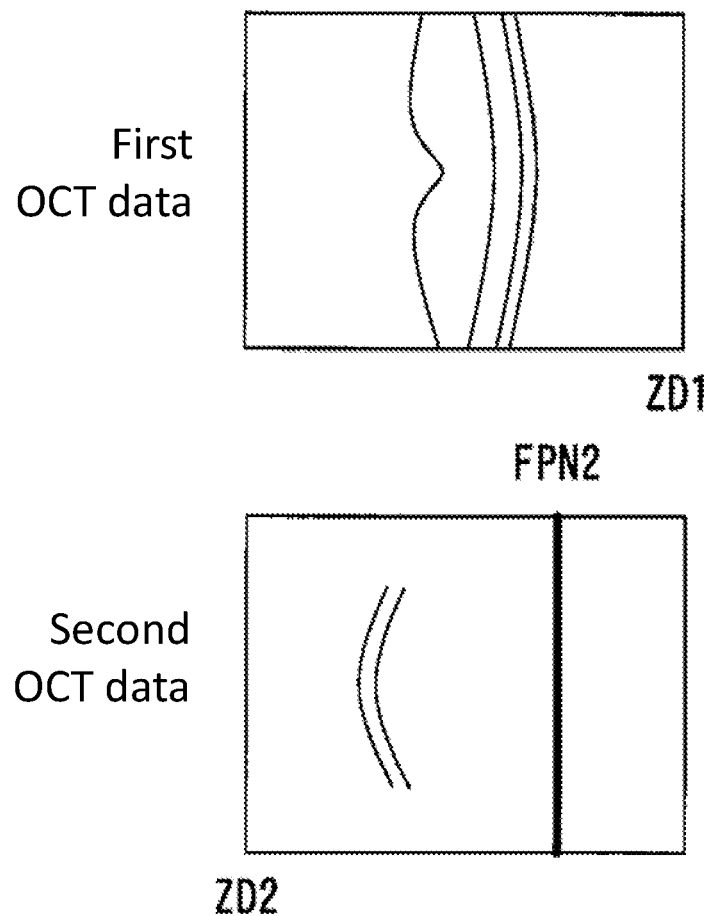
FIG. 13 is a diagram showing an example of a case of applying real-time correction in the fundus imaging mode.

FIG. 13 is a diagram showing an example of a case of applying real-time correction in the fundus imaging mode. For example, the control unit 70 adjusts the optical path length of at least one of the measurement light and the reference light and sets an acquisition region of the OCT data in the fundus by one of the first detector 120*a* and the second detector 120*b* (refer to the fundus imaging mode described above).

In addition, the control unit 70 sets an acquisition region of the OCT data on an optical member (for example, the optical member 204 or the optical member 206) of the FPN generating optical system 200 by the other of the first detector 120*a* and the second detector 120*b*. In this case, an optical path length of the FPN generating optical system 200 is set to a length different from the optical path length of the measurement light reaching the first detector 120*a* through the fundus. For example, the control unit 70 may adjust the optical path length difference between the measurement light and the reference light such that the optical path length of the reference light having passed through at least any one of the plurality of reference optical paths matches the optical path length of the measurement light having passed through the FPN generating optical system 200.

For example, in the example, the optical member disposed on the measurement optical path may be moved such that the optical path length of the measurement light from the fundus matches that of the reference light from the first reference optical path 110*a*, and thereby the optical path length of the measurement light may be adjusted. Consequently, the OCT data of the fundus is included in the first OCT data that is obtained based on the output signal from at least the first detector 110a.

In addition, in a state in which the position of the optical member disposed on the measurement optical path is adjusted such that the OCT data of the fundus is included in the first OCT data, the control unit 70 may move the optical member 112 disposed on the second reference optical path 110b such that the optical path length of the measurement light from the optical member of the FPN generating optical system 200 matches that of the reference light from the second reference optical path 110b, and thereby the control unit 70 may adjust the optical path length of the reference light of the second reference optical path 110b, for example. Consequently, the OCT data of the FPN signal is included in the second OCT data that is obtained based on the output signal from the second detector 110b. In this case, as a result, a signal of the cornea, the crystalline lens, or the like, in addition to the FPN signal, may be included.

In the above description, the application example of the fundus imaging mode is described; however, the configuration described above is not limited thereto, and the configuration described above may be applied to the other imaging modes.

Alignment Detection Using OCT Signal

For example, the control unit 70 may adjust the optical path length of at least one of the measurement light and the reference light, set an acquisition region of the OCT data in the anterior chamber including at least one of the cornea and the pupil (or the iris) by one of the first detector 120a and the second detector 120b, and detect relative positional information of the apparatus main body with respect to the examinee's eye based on a position of a characteristic site on the OCT data. In this case, since the optical path length difference between the measurement light and the reference light in the OCT optical system 100 can be acquired in advance (may be stored in a memory in advance, or may be detected based on the position or the like of the optical member), the known zero-delay position is used, the position of the characteristic site with respect to the zero-delay position is detected, and thereby it is possible to detect the relative positional information of the apparatus main body with respect to the examinee's eye.

For example, as the relative positional information, an operation distance of the apparatus main body with respect to the examinee's eye may be detected, distances of the apparatus main body in right, left, upward, and downward directions thereof with respect to the examinee's eye may be detected, or a position of the apparatus main body with respect to the examinee's eye may be three-dimensionally detected. In this case, an appropriate deviation amount from an alignment position may be detected, for example.

For example, the control unit 70 may analyze the OCT data of the anterior chamber so as to detect a position of the characteristic site (for example, a vertex of the cornea or the center of the pupil) of the examinee's eye and perform automatic alignment for automatically moving the apparatus main body with respect to the detected characteristic site. In this case, the control unit 70 may detect the position of the characteristic site three-dimensionally and perform the three-dimensional automatic alignment with respect to the detected characteristic site. Consequently, since it is possible to detect a three-dimensional position by the OCT data with high accuracy, it is possible to perform alignment with respect to the examinee's eye with high accuracy.

For example, in a case where the characteristic site is detected, image processing such as edge detection may be performed. Then, an image region corresponding to the characteristic site may be searched, and a position, at which the image region corresponding to the characteristic site is detected, may be detected as the position of the characteristic site. In automatic alignment control, a drive mechanism for moving the apparatus main body three-dimensionally may be provided.

In a case where alignment detection using the OCT signal is performed, the fundus may be set as the acquisition region of the OCT data by the other of the first detector 120a and the second detector 120b. Consequently, it is possible to perform the alignment with respect to the fundus with high accuracy. Otherwise, the control unit 70 may detect the relative positional information of the apparatus main body with respect to the fundus of the examinee's eye by using the relative positional information of the apparatus main body with respect to the anterior chamber which is detected as described above and the optical path length difference between the first reference optical path 110a and the second reference optical path 110b. In this case, the position of the fundus on the OCT data may be detected. In addition, the imaging site is not limited to the fundus, and an imaging site other than the fundus may be set as the acquisition region of the OCT data by the other of the first detector 120a and the second detector 120b, or the crystalline lens may be set, for example.

Polarization Adjustment

The control unit 70 may control a polarization adjusting unit (for example, a first polarization adjusting unit 300, a second polarization adjusting unit 302, or a third polarization adjusting unit 304) so as to adjust a polarization state when the OCT data is obtained. For example, as a timing of adjustment of the polarization state, the adjustment may be executed at the time of power-on or may be executed whenever an examinee is changed. In addition, the adjustment may be executed at the time of optimization control for optimizing imaging conditions in the OCT optical system.

Figure 14:
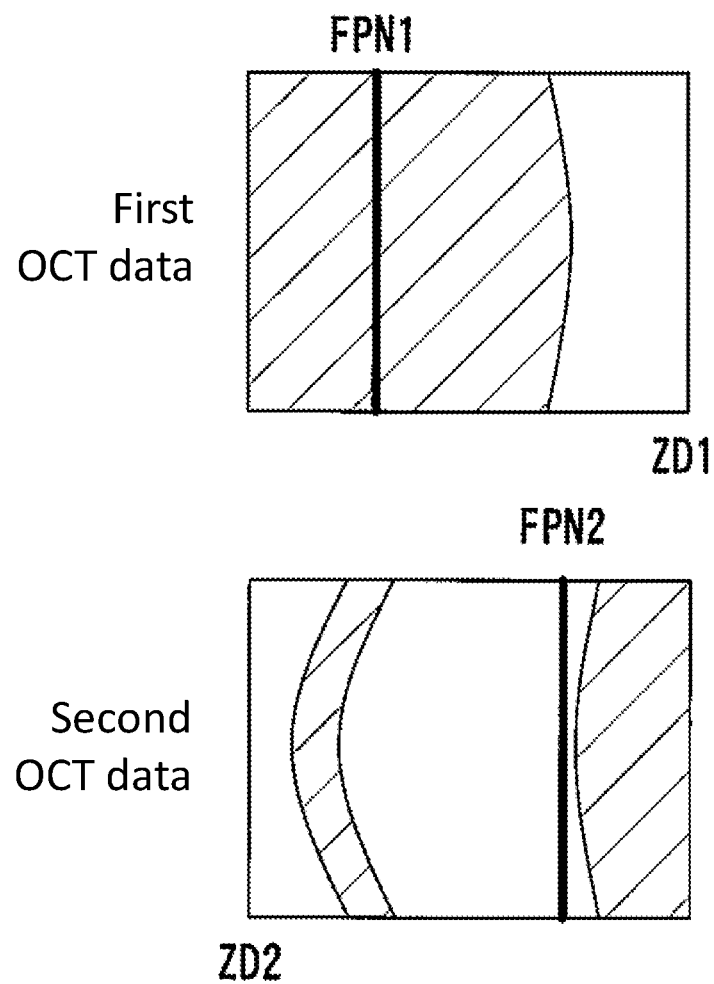
FIG. 14 is a diagram showing an example of OCT data acquired in a case of performing polarization adjustment in the anterior chamber imaging mode.

Hereinafter, an example of the adjustment of the polarization state in the anterior chamber imaging mode will be described. FIG. 14 is a diagram showing an example of the OCT data acquired in a case of performing the polarization adjustment in the anterior chamber imaging mode. First, the control unit 70 controls the second polarization adjusting unit 302 and adjusts the polarization state such that the maximum signal intensity of the cornea image in the second OCT data is achieved. Consequently, the cornea image in the second OCT data is acquired with high signal intensity.

Figure 15:
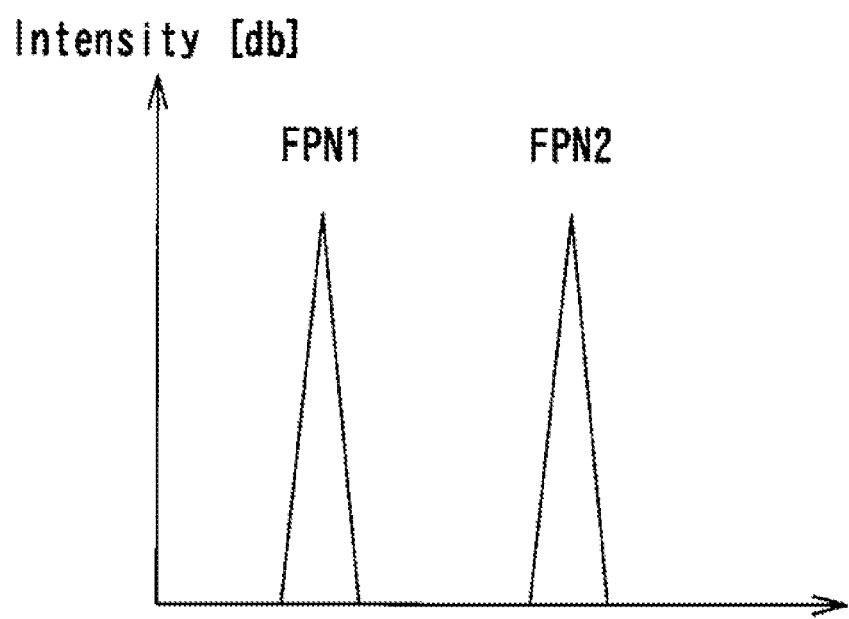
FIG. 15 is a graph showing an example of a signal intensity of the FPN.

FIG. 15 is a graph showing an example of the signal intensity of the FPN. Next, the control unit 70 controls the third polarization adjusting unit 304 and adjusts the polarization state such that the maximum signal intensity of the FPN signal in the second OCT data is achieved. Consequently, the FPN signal in the second OCT data is acquired with high signal intensity. As a result, the cornea image and the FPN signal in the second OCT data are acquired with high signal intensity.

Next, the control unit 70 controls the first polarization adjusting unit 300 and adjusts the polarization state such that a signal intensity ratio between the FPN signal in the second OCT data and the FPN signal in the first OCT data is equal to a predetermined signal intensity ratio (for example, a state in which the signal intensity ratios are equal to each other). Consequently, the FPN signal in the first OCT data is acquired with high signal intensity, and the crystalline lens image in the first OCT image is acquired with high signal intensity.

According to the control described above, it is possible to adjust a balance of the signal intensity between the first OCT data and the second OCT data. Further, by using the signal intensity ratio between the FPN signal in the second OCT data and the FPN signal in the first OCT data in adjusting the polarization state related to the OCT data including the crystalline lens, the polarization state is adjusted with higher accuracy than the polarization state is adjusted by using the crystalline lens image. That is, there is a possibility that the crystalline lens image in this case will be limited only to information of the crystalline lens rear surface. Therefore, an amount of information as an image is relatively small, and thus there is a possibility that the accuracy as a signal evaluation value will decrease. As a result, it is not possible to smoothly adjust the polarization state, in some cases. By contrast, since it is possible to secure stable signal intensity by using the FPN signal, it is possible to secure the accuracy as the signal evaluation value, and thus it is possible to smoothly adjust the polarization state.

In addition, a polarization state of the FPN generating optical system is adjusted, and thereby it is possible to detect the FPN signal with high accuracy. Therefore, it is possible to appropriately perform various processes using the FPN signal.

In the above description, the polarization state related to the OCT data including the crystalline lens is adjusted by using the FPN signal; however, the adjustment is not limited thereto, and the polarization state may be adjusted by using the signal intensity of the crystalline lens image in the OCT data.

In the above description, in a case of using the first detector 120*a* and the second detector 120*b*, the polarization state related to each of the OCT data that is obtained by the first detector 120*a* and the OCT data that is obtained by the second detector 120*b* is adjusted, and thereby it is possible to acquire each of the OCT data with high signal intensity. It is needless to say that the adjustment is not limited thereto, and the polarization state only related to one item of the OCT data may be adjusted.

In addition, in a case of using one of the first detector 120*a* and the second detector 120*b*, the polarization state related to the OCT data that is obtained by a detector that is used may be adjusted.

Example of Light Guiding Optical System

Here, an example of the light guiding optical system 150 is described with reference to FIGS. 16A and 16B.

Figure 16A:
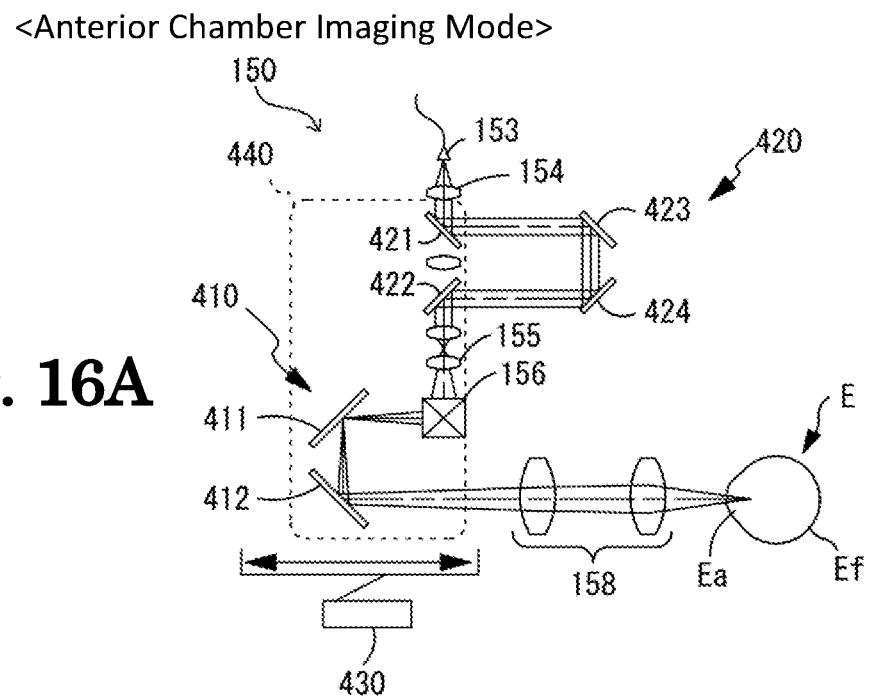
FIGS. 16A and 16B are diagrams for describing a switching operation of optical disposition in a light guiding optical system.
Figure 16B:
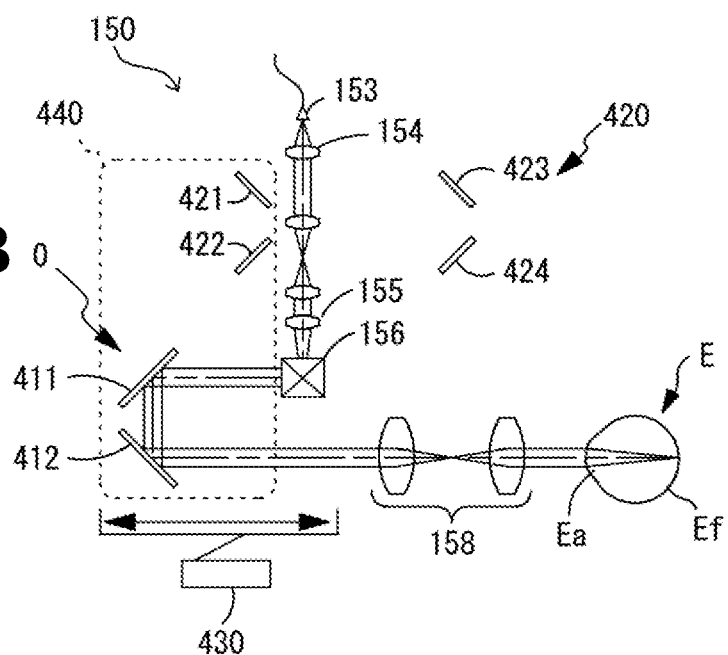

The optical disposition of the light guiding optical system 150 shown in FIGS. 16A and 16B is switched depending on a depth position to be imaged. To be more specific, as a switching unit that switches a mode in the light guiding optical system 150 between the fundus imaging mode and the anterior chamber imaging mode, a first switching unit 410 and a second switching unit 420 are provided.

As an example, the first switching unit 410 shown in FIGS. 16A and 16B includes mirrors 411 and 412 and moves the mirrors 411 and 412, thereby changing the optical path length between an objective optical system 158 and an optical scanner 156 (FIG. 16A↔FIG. 16B). As a result of changing the optical path length between the objective optical system 158 and the optical scanner 156, a relative position of a focal point in the objective optical system 158 and the optical scanner 156 is switched.

The mirrors 411 and 412 in the first switching unit 410 shown in FIGS. 16A and 16B are disposed on a stage 440 and are moved when a drive unit 430 drives the stage 440, and the optical path length between the objective optical system 158 and the optical scanner 156 is changed. The drive unit 430 is driven by the control unit 70. In response to the change of the optical path length, the relative position is switched between two positions of a first position (position at which the optical scanner 156 is disposed to be substantially coincident with the focal point of the objective optical system 158, refer to FIG. 16A) and a second position (position at which the optical scanner 156 and the anterior chamber have a conjugated relationship with respect to the objective optical system 158, refer to FIG. 16B).

In a case where the relative position is the first position, an examinee's eye E is irradiated with the measurement light having passed through the objective optical system 158 through the optical scanner 156, the beam as a telecentric beam or a near-telecentric beam on a side of an object. As a result, it is possible to acquire the OCT data in a wide range of an anterior chamber Ea.

In the example, the first position is a position at which the optical scanner 156 is disposed to be slightly separated from a position of the focal point of the objective optical system 158 (a focal point on the side of the light source). As a result, the measurement light is emitted from the objective optical system 158 toward the examinee's eye E, with the main ray thereof being inclined to an approaching direction toward the optical axis.

In this case, in the example, a range of an angle of the main ray of the measurement light with respect to the optical axis is set between the following first angle and second angle. The first angle is an angle formed between the optical axis and a first main ray as a main ray which matches one of normal lines of the sphere having a cornea-equivalent radius (for example, 7.8 mm) and placed at an appropriate operation distance. In addition, the second angle is an angle formed between the optical axis and a second main ray as a main ray which matches one of normal lines of the sphere having a sclera-equivalent radius (for example, 14 mm) and placed at an appropriate operation distance.

As a result, a component more approximate to specular reflection (that is, a larger amount of beam) of the measurement light reflected or scattered by the cornea, the sclera, or both thereof can be collected as return beams and be received by the detectors 120*a* and 120*b*. As a result, it is possible to obtain the OCT data of the anterior chamber with high intensity in the cornea, the sclera, or both thereof in a wide range of the anterior chamber Ea.

In addition, in a case where the relative position of the focal point in the objective optical system 158 and the optical scanner 156 is the second position, the fundus is irradiated with the measurement light having passed through a point of the anterior chamber and the pupil. As a result, the OCT data of the fundus is smoothly acquired.

As described above, the relative position of the focal position in the objective optical system 158 and the optical scanner 156 is switched by the first switching unit 410, and thereby it is possible to acquire the OCT data in each of the anterior chamber and the fundus.

Here, in the example, the objective optical system 158 has a positive curve that causes the concentrating plane to curve into a convex shape toward the side of the fundus (refer to FIG. 17). Consequently, in the mode switching method of the embodiment of switching the relative position of the focal point in the objective optical system 158 and the optical scanner 156 and switching the imaging mode, it is easy to obtain both the anterior chamber OCT and the fundus OCT in a wide range.

For example, in a case where the relative position of the focal point in the objective optical system 158 and the optical scanner 156 is the first position, the curvature radius (R) of the concentrating plane may be appropriately selected such that the concentrating position is smoothly set with respect to each of the crystalline lens and the anterior chamber angle which are at different depths from each other in a range of R≤28.5 mm. Consequently, it is possible to obtain the OCT data of the anterior chamber with high image quality or resolution in a wide range in directions of the depth direction and the transverse direction.

In addition, in a case where the relative position of the focal point in the objective optical system 158 and the optical scanner 156 is the first position, the curvature radius (R) of the concentrating plane may be appropriately selected so as to match the curve of the fundus. In this case, it is possible to obtain good fundus OCT data in a wide range. It is more preferable that the curvature radius of the concentrating plane does not change at the time of imaging the anterior chamber and at the time of imaging the fundus, because it is also possible to achieve a preferred configuration of obtaining an image of the fundus, in addition to the anterior chamber, when R≤21 as described above.

In the example, when the relative position is switched between the first position and the second position, the concentrating position adjusting optical system is linked and driven. In the example, the concentrating position adjusting optical system is a refractive power changeable lens (for example, a liquid crystal lens) 155 provided between the optical scanner 156 and the coupler of the OCT optical system. In a case where the relative position is the first position, the control unit 70 adjusts the refractive power of the refractive power changeable lens 155 such that the concentrating plane is formed in the anterior chamber. For example, the refractive power in this case may be predetermined. In addition, in a case where the relative position is the second position, the control unit 70 adjusts the refractive power of the refractive power changeable lens 155 such that the concentrating plane is formed in the fundus. The refractive power at the second position may be set individually for each examinee's eye E, with consideration for diopter for each examinee's eye E.

In a case where the relative position of the focal point in the objective optical system 158 and the optical scanner 156 is switched by the first switching unit 410, the optical path length difference between the measurement optical path and the reference optical path changes. By contrast, in FIGS. 16A and 16B, at least a part of a change in optical path length difference is offset by the second switching unit 420.

In FIGS. 16A and 16B, the second switching unit 420 includes mirrors 421 to 424. The second switching unit 420 switches a state between a retraction state in which the mirrors 421 to 424 retract from the measurement optical path and an insertion state of being disposed on the measurement optical path. Of the mirrors 421 to 424, the mirrors 421 and 422 are disposed on the stage 440, the drive unit 430 drives the stage 440, and thereby the mirrors are inserted and removed with respect to the measurement optical path. The mirrors 421 and 422 are inserted on the measurement optical path, and thereby the mirrors 421 to 424 form a detour optical path. This results in an increase in optical path length between a coupler 153 and the optical scanner 156 more than before the insertion. As described above, the second switching unit 420 changes the optical path length of the measurement optical path between the optical scanner 156 and the coupler 153.

Here, the mirrors 411 and 414 of the first switching unit 410 and the mirrors 421 and 422 of the second switching unit 420 are disposed on the one stage 440, and thus the mirrors 411, 414, 421, and 422 are integrally displaced. In this manner, the first switching unit 410 and the second switching unit 420 are linked to each other. That is, in a case where an optical path between the optical scanner 156 and the examinee's eye E is shortened by the first switching unit 410, the detour optical path is formed by the mirrors 421 to 424 in the second switching unit 420. As a result, an optical path from the optical scanner 156 to the coupler 153 is extended (FIG. 16B→FIG. 16A). In this case, the optical path length difference between the measurement optical path and the reference optical path is increased before and after the drive of the stage 440. As a result, it is possible to omit or simplify the adjustment of a reference optical system after the drive. Conversely, in a case where the optical path between the optical scanner 156 and the examinee's eye E is shortened by the first switching unit 410, detour of the measurement light is canceled in response to retraction of the mirrors 421 and 422 from the measurement optical path, in the second switching unit 420. As a result, an optical path from the optical scanner 156 to the coupler 153 is shortened (FIG. 16A→FIG. 16B). In this case, the optical path difference between the measurement optical path and the reference optical path is decreased before and after the drive of the stage 440. As a result, it is possible to omit or simplify the adjustment of the reference optical system after the drive. In addition, since the second switching unit 420 adjusts the optical path by two folded optical paths, a drive amount is reduced, and this contributes to compactness of the apparatus.

As described above, the change in optical path length (in other words, a change in optical path length difference between the measurement optical path and the reference optical path) in the measurement optical path in response to a change in position of the turning point by the first switching unit 410 is reduced by the second switching unit 420.

In FIGS. 16A and 16B, for example, the mirrors 411 and 412 in the first switching unit 410 and the mirrors 421 to 424 in the second switching unit 420 may be replaced with prisms or the like.

Noise Removing Process

A noise removing process may be performed on the OCT data of the anterior chamber which is acquired as described above. For example, in the example, the noise removing process is executed by DC subtraction on a region excluding the crystalline lens region of the OCT data of the anterior chamber.

Spectral data acquired by irradiating the crystalline lens with the measurement light in a depth region in which the crystalline lens is positioned (a deeper region than the iris) is distinguished from other spectral data (that is by irradiating the iris or the anterior chamber angle), a DC component is identified by only the other spectral data, and noise removal by the DC subtraction is performed. Noise removal by the DC subtraction may be performed by using entire spectral data for each scanning position in a region positioned shallower than the iris. Consequently, it is possible to obtain the OCT data of the anterior chamber, an S/N ratio of the OCT data being more improved.

Example Corresponding to Altered Embodiment

An example corresponding to the altered embodiment is described with reference to FIG. 18. For convenience, the light guiding optical system 150 when the anterior chamber imaging mode (refer to FIG. 16A) is set in the example is described as an optical system of the apparatus main body. In this state, an attachment optical system 600 is attached and detached between the objective optical system 158 and the examinee's eye E, and thereby the OCT data of the fundus is smoothly acquired. In addition, although will be described below in detail, it is easy to decrease a change in optical path length difference in response to the attachment and detachment in a case of using the attachment optical system 600.

Figure 18:
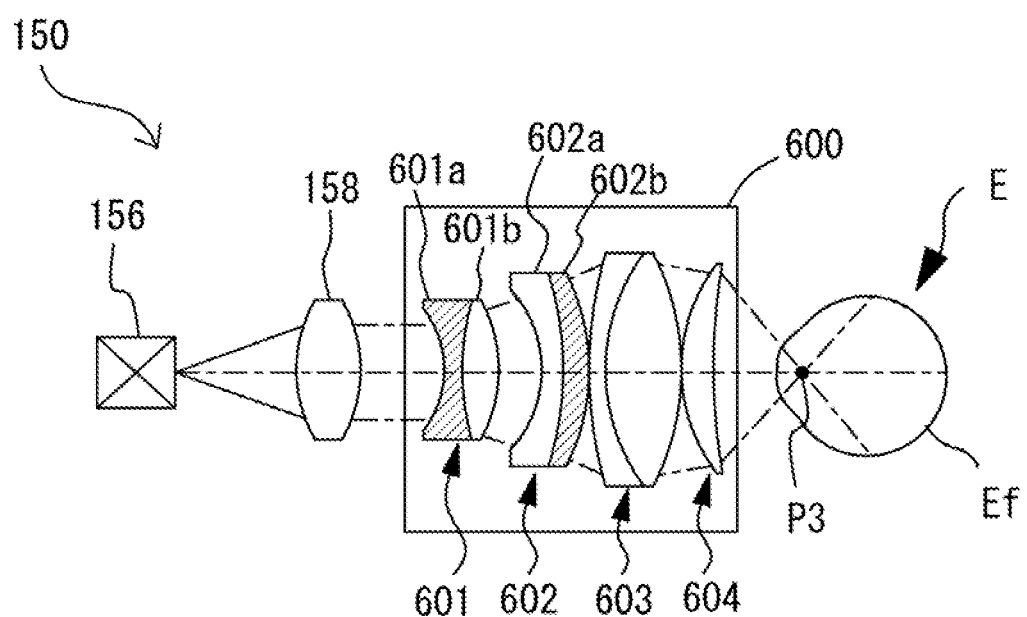
FIG. 18 is a diagram for describing an OCT apparatus according to an altered embodiment.

With reference to FIG. 18, an optical system when the attachment optical system 600 is attached and detached is described. FIG. 18 shows the light guiding optical system 150 in an installed state of the attachment optical system 600.

In FIG. 18, similarly to the anterior chamber imaging mode (refer to FIG. 16A), the light guiding optical system 150 is disposed such that the focal point of the objective optical system 158 matches the optical scanner 156. Therefore, the measurement light is emitted from the objective optical system 158 toward the examinee's eye E, as a telecentric beam flux with respect to the optical axis L of the measurement optical path. The measurement light is guided toward the examinee's eye E through the inspection window and the attachment optical system 600. The attachment optical system 600 has the positive power and forms a turning point P of the measurement light as a whole. The pupil position of the examinee's eye E matches the turning point P, and thereby scanning with the measurement light is to be performed on the fundus. As described above, the attachment optical system 600 bends the telecentric beam flux in the inspection window toward the optical axis L such that the beam flux has an expected angle.

Incidentally, as the maximum value of the ray height of the measurement light increases more inside the attachment optical system, the operation distance during installation can be set to be more longer. Here, in an optical system as described in "JP-A-2016-123467", measurement light that is emitted from an objective optical system necessarily faces toward the optical axis once on a way of being incident to the attachment optical system, and thus an optical path length in the attachment optical system is likely to be elongated in order to obtain an expected ray height.

By contrast, in the optical system shown in FIG. 18, a telecentric beam flux is incident to the attachment optical system 600 from the apparatus main body. Hence, it is easy for the attachment optical system 600 to cause the beam flux to reach the expected ray height by a shorter distance (optical path length). Consequently, it is possible to decrease the attachment optical system 600 in size. In addition, it is relatively easy to suppress a change in optical path length of the measurement optical path in response to the attachment and detachment (insertion and removal) of the attachment optical system 600. As a result, the adjustment of the OPL is advantageously performed in response to the attachment and detachment (insertion and removal) of the attachment optical system 600. To be more specific, there are found advantages in that it is easy to simplify a configuration for the adjustment of the OPL or it is possible to more quickly complete the adjustment of the OPL.

The attachment optical system 600 includes a first lens 601, a second lens 602, a third lens 603, and a fourth lens 604. The first lens 601, the second lens 602, the third lens 603, and the fourth lens 604 are arranged in this order from the objective optical system 158 toward the examinee's eye E. The first lens 601 belongs to the first lens group in the example, and the second lens 602 to the fourth lens 604 belong to the second lens group in the example. The first lens 601 is a principal lens that increases the ray height for securing the operation distance. The second lens 602 mainly distributes to a reduction in aberration. The third lens 603 and the fourth lens 604 are principal lenses that bend the measurement light toward the optical axis L (in other words, a lens having the principal positive power in the attachment optical system 600).

The first lens 601 has the negative power and increases the ray height of the measurement light emitted from the objective optical system 158. In addition, the first lens 601 reduces an occurrence of asymmetrical aberration and field distortion. To be more specific, the first lens 601 has a lens front surface and a lens rear surface having a convex meniscus shape toward the side of the examinee's eye. The meniscus shape suppresses an occurrence of the asymmetrical aberration such as a coma aberration and astigmatism with respect to the optical axis L.

In addition, the first lens 601 is the compound lens in which two spherical lenses of a concave lens 601a and a convex lens 601b are joined. Of the lenses 601a and 601b, the concave lens 601a is formed of a material having a higher refractive index. Consequently, it is easy to smoothly increase the ray height.

Similarly to the first lens 601, the second lens 602 has a lens front surface and a lens rear surface having a convex meniscus shape toward the side of the examinee's eye. Accordingly, also by the second lens 602, an occurrence of the asymmetrical aberration with respect to the optical axis L is suppressed. In addition, in the second lens 602, a concave lens 602a and a convex lens 602b are joined. Of the lenses 602a and 602b, the convex lens 602b is formed of a material having a higher refractive index. That is, of the convex lens and the concave lens that form the compound lens, one formed of the material having the higher refractive index is different between the first lens 601 and the second lens 602. Consequently, at least a part of a curve occurring by the first lens 601 is offset by the second lens 602. As a result, the distortion occurring in the attachment optical system 600 is suppressed.

In addition, the aberration suppressing effect of the first lens 601 and the second lens 602 may be more weighted on the curved field than the chromatic aberration. In this case, a condition that the two compound lenses need to satisfy is represented by Expression (6) as described above.

$$\frac{N_{1p}f_{1p} + N_{1n}f_{1n}}{N_{2p}f_{2p} + N_{2n}f_{2n}} > \frac{N_{1p}N_{1n}|f_{1p} + f_{1n}|}{N_{2p}N_{2n}|f_{2p} + f_{2n}|} \tag{6}$$

Here, N represents a refractive index of a lens, and f represents a focal length of a lens. 1p as an index represents a value of the convex lens 601a, 1n represents a value of the concave lens 601b, 2p represents a value of the convex lens 602a, and 2n represents a value of the concave lens 602b.

Modification Example

As described above, this disclosure is described, based on the embodiments and the altered embodiments; however, this disclosure is not limited to the embodiments and the altered embodiments described above, and it is possible to perform various modifications thereof.

For example, in the above description, the SS-OCT is described as an example; however, the example is not limited thereto, and the technology of this disclosure may be applied to SD-OCT. In this case, a plurality of spectrometers may be used as the plurality of detectors.

In addition, the OCT apparatus of the embodiment and the altered embodiment may employ a configuration of PS-OCT. The PS-OCT is polarization sensitive OCT and is capable of acquiring at least any one of birefringence of an inside of an examinee's eye (retardation), a polarization axis (axis orientation), double attenuation (die attenuation) and the like.

In addition, in the above description, the OCT apparatus for imaging the examinee's eye is described as an example; however, the technology is not limited thereto, and the technology of this disclosure may be applied to an OCT apparatus for imaging OCT data of a subject, for example. In addition, the subject may be a material other than a living organism, in addition to a living organism such as an eye (the anterior chamber, the fundus, or the like) or skin.

What is claimed is:

1. An OCT apparatus comprising:
   an OCT optical system that causes an optical splitter to split light from an OCT light source into a measurement optical path and a reference optical path, and detects a spectral interference signal between measurement light guided to an examinee's eye through the measurement optical path and reference light from the reference optical path;
   an image processor that processes the spectral interference signal output from the OCT optical system to acquire OCT data of the examinee's eye;
   an optical scanner that deflects the measurement light from the optical splitter, and performs scanning on tissue of the examinee's eye; and
   a light guiding optical system that includes an objective optical system, guides the measurement light from the optical splitter to the examinee's eye through the objective optical system, and forms a concentrating plane of the measurement light in an anterior chamber of the examinee's eye,
   wherein the objective optical system curves the concentrating plane such that the concentrating plane has a convex shape toward a side of a fundus of the examinee's eye,
   the optical scanner is disposed at a position separated from the objective optical system by a distance longer than a focal length of the objective optical system,
   a main ray of the measurement light as emitted from the objective optical system to the examinee's eye is inclined in an approaching direction toward an optical axis of the light guiding optical system, and
   the objective optical system guides the measurement light having passed through the optical scanner to the concentrating plane without causing the measurement light to intersect an optical axis of the measurement optical path, and concentrates the measurement light on the concentrating plane.

2. The OCT apparatus according to claim 1,
   wherein the objective optical system has a positive curvature for curving the concentrating plane in a range where a curvature radius of the concentrating plane is 28.5 mm or smaller.

3. The OCT apparatus according to claim 1,
   wherein the objective optical system has one or more lenses.

4. The OCT apparatus according to claim 1,
   wherein an angle of the main ray with respect to the optical axis is set in a range of a first angle or smaller, the first angle being formed between the optical axis and a first main ray that matches a normal line of a sphere having a cornea-equivalent radius and placed at an appropriate operation distance.

5. The OCT apparatus according to claim 1,
   wherein an angle of the main ray with respect to the optical axis is set in a range of a second angle or larger, the second angle being formed between the optical axis and a second main ray that matches a normal line of a sphere having a sclera-equivalent radius and placed at an appropriate operation distance.

6. The OCT apparatus according to claim 1, further comprising:
   a switching unit configured to perform mode switching of the light guiding optical system between an anterior chamber imaging mode in which the concentrating plane of the measurement light from the optical scanner is formed in the anterior chamber of the examinee's eye and a fundus imaging mode in which the optical scanner and a pupil of the examinee's eye are disposed at a conjugated position,
   wherein the switching unit performs the mode switching by a first method of changing a positional relationship between a focal point of the objective optical system and the optical scanner, a second method of inserting and removing a lens into and from the objective optical system, and a third method of combining both the first method and the second method.

7. The OCT apparatus according to claim 6,
   wherein the curvature of the concentrating plane is maintained in the convex shape toward the side of the fundus of the examinee's eye in a state where the switching unit has switched from the anterior chamber imaging mode to the fundus imaging mode.

8. The OCT apparatus according to claim 6,
   wherein the OCT optical system includes a plurality of the reference optical paths having different optical path lengths from each other.

9. The OCT apparatus according to claim 6, further comprising:
   an optical path length difference adjusting unit configured to adjust an optical path length difference between the measurement optical path and the reference optical path in response to the mode switching by the switching unit.

10. The OCT apparatus according to claim 6,
    wherein the objective optical system guides the measurement light having passed through the optical scanner to a first concentrating plane without causing the measurement light to intersect an optical axis of the measurement optical path, and concentrates the measurement light on the first concentrating plane,
    the switching unit includes an attachment optical system that is inserted and removed on the measurement optical path between the objective optical system and the examinee's eye, and
    the attachment optical system is inserted on the measurement optical path to bend the measurement light having passed through the objective optical system toward a side of the optical axis, to form a turning point of the measurement light at a conjugated position of the optical scanner with respect to the objective optical system and the attachment optical system, and to concentrate the measurement light having passed through the turning point on a second concentrating plane.

11. The OCT apparatus according to claim 10, wherein the attachment optical system bends the measurement light toward the side of the optical axis such that a second solid angle that is a scanning solid angle of the measurement light at the turning point is greater than a first solid angle that is a scanning solid angle of the measurement light in the optical scanner.

12. The OCT apparatus according to claim 10, wherein the attachment optical system is a lens attachment including one or more lenses.

13. The OCT apparatus according to claim 12, wherein the attachment optical system includes a first lens group having negative power and a second lens group having positive power, the first lens group and the second lens group being arranged in this order from the objective optical system toward the examinee's eye.

14. The OCT apparatus according to claim 13, wherein the attachment optical system includes a compound lens that is suitable for correcting at least one of an asymmetrical aberration and a curved field and is obtained by joining a lens having negative power and a lens having positive power, the compound lens being provided in one of the first lens group and the second lens group or in a part of each of the lens groups.

* * * * *